United States Patent

Condie et al.

[11] Patent Number: 5,902,325
[45] Date of Patent: May 11, 1999

[54] METHOD AND APPARATUS FOR DETECTING CARDIAC CAPTURE

[75] Inventors: Catherine R. Condie, Minneapolis; Daniel J. Baxter, St. Paul; William J. Combs, Eden Prairie; Daniel J. Greeninger, Coon Rapids; Karen J. Kleckner, New Brighton; H. Toby Markowitz, Roseville; John C. Stroebel, Blaine; John D. Wahlstrand, Shoreview, all of Minn.

[73] Assignee: Medtronic, Inc., Minneapolis, Minn.

[21] Appl. No.: 09/126,469

[22] Filed: Jul. 30, 1998

Related U.S. Application Data

[62] Division of application No. 08/784,687, Jan. 22, 1997, Pat. No. 5,843,137, which is a division of application No. 08/346,815, Nov. 30, 1994, Pat. No. 5,713,933.

[51] Int. Cl.⁶ ........................................ A61N 1/37
[52] U.S. Cl. .................................................. 607/28
[58] Field of Search ........................................ 607/28

[56] References Cited

U.S. PATENT DOCUMENTS

| | | | |
|---|---|---|---|
| 4,337,776 | 7/1982 | Daly et al. | 607/28 |
| 4,899,750 | 2/1990 | Ekwall | 607/28 |
| 5,003,975 | 4/1991 | Hafelfinger et al. | 607/28 |
| 5,713,933 | 2/1998 | Condie et al. | 607/28 |

*Primary Examiner*—William E. Kamm
*Attorney, Agent, or Firm*—Harold R. Patton; Michael B. Atlass

[57] ABSTRACT

A method and apparatus for automatic determination of a pacemaker patient's pacing stimulation threshold. Circuitry is provided in a pacemaker for obtaining a signal reflecting cardiac impedance, which is known to reliably reflect certain aspects of cardiac function. Circuitry is also provided for monitoring the cardiac impedance waveform during a predetermined capture detect window following delivery of stimulating pulses. One or more values are derived which characterize the morphology of the impedance waveform during the capture detect window associated with each stimulation pulse delivered. These values are compared to predetermined control values in order to assess whether a stimulation pulse has achieved cardiac capture. The assessment of whether cardiac capture has been achieved is also based partly upon the conventional sensing of atrial and/or ventricular cardiac signals occurring during the capture detect window. In one embodiment of the invention, the control values against which impedance waveform characterization values are compared are obtained by delivering a series of stimulation pulses having sufficient energy to ensure that capture is achieved, and by monitoring the impedance waveform during delivery of these pulses.

7 Claims, 14 Drawing Sheets

LOSS OF CAPTURE INDICATED BY IMPEDANCE

LOSS OF CAPTURE INDICATED BY A SENSE

METHOD AND APPARATUS FOR DETECTING CARDIAC CAPTURE

This is a Divisional Application of U.S. application Ser. No. 08/784,687, filed Jan. 22, 1997 now U.S. Pat. No. 5,843,137, which itself is a divisional of U.S. application Ser. No. 08/346,815 filed Nov. 30, 1994 now issued as U.S. Pat. No. 5,713,933.

FIELD OF THE INVENTION

This invention relates to the field of implantable medical devices, and more particularly relates to a method and apparatus for determining pacing threshold levels for an implantable pacemaker.

BACKGROUND OF THE INVENTION

In general, cardiac pacemakers are electrical devices used to supplant some or all of an abnormal heart's natural pacing function. Pacemakers typically operate to deliver appropriately timed electrical stimulation signals, sometimes called pacing pulses, designed to cause the myocardium to contract or "beat." For state-of-the-art pacemakers, the rate at which stimulation signals are delivered may be variable, and such variation may occur automatically in response to detected changes in a patient's level of physical activity. Such rate- or activity-responsive pacemakers depend on physiologically-based signals, such as signals from sensors measuring the pressure inside the patient's ventricle, for determining a patient's activity level. One popular method for measuring a patient's activity level, and hence the patient's demand for oxygenated blood, is to measure the physical activity of the patient by means of a piezoelectric transducer. Such a pacemaker is disclosed in U.S. Pat. No. 4,485,813 to Anderson et al.

In typical prior art rate-responsive pacemakers, the pacing rate is determined according to the output from an activity sensor. The pacing rate is variable between a predetermined maximum and minimum level, which may be selectable by a physician from among a plurality of programmable upper and lower rate limit settings. When the activity sensor output indicates that the patient's activity level has increased, the pacing rate is increased from the programmed lower rate by an incremental amount which is determined as a function of the output of the activity sensor. That is, the rate-responsive or "target" pacing rate in a rate-responsive pacemaker is determined as follows:

Target Rate=Programmed Lower Rate+$f$(sensor output)

where f is typically a linear or monotonic function of the sensor output. As long as patient activity continues to be indicated, the pacing rate is periodically increased by incremental amounts until the rate computed according to the above formula is reached (or until the programmed upper rate limit is reached, whichever is lower). In this way, an elevated pacing rate (i.e., one higher than the programmed lower rate limit) may be sustained during periods of patient activity. When patient activity ceases, the pacing rate is gradually reduced, until the programmed lower rate limit is reached.

For any of the known rate-responsive pacemakers, it is clearly desirable that the sensor output correlate to as high a degree as possible with the actual metabolic and physiologic needs of the patient, so that the resulting rate-responsive pacing rate may be adjusted to appropriate levels. A piezoelectric activity sensor can only be used to indirectly determine the metabolic need. The physical activity sensed can be influenced by upper body motion. Therefore, an exercise that involves arm motion may provide signals that are inappropriately greater than the metabolic need. Conversely, exercises that stimulate the lower body only, such as bicycle riding, may provide a low indication of metabolic need while the actual requirement is very high.

To address these perceived disadvantages in the prior art, other physiologically-based parameters have been utilized to assess a patient's metabolic demand. Among these parameters are cardiac pressure, blood oxygen saturation, and minute ventilation ($V_e$), each of which having been demonstrated clinically to be parameters that correlates well with the actual metabolic and physiologic needs of the patient.

Minute ventilation, which has been found to be a very good indicator of a patient's metabolic demand, is defined by the equation:

$$V_e = RR \times VT$$

where RR=respiration rate in breaths per minute (bpm), and VT=tidal volume in liters. Clinically, the measurement of $V_e$ is performed by having the patient breathe directly into a device that measures the exchange of air and computes the total volume per minute. The direct measurement of $V_e$ is not practical with an implanted device. However, measurement of the impedance changes of the thoracic cavity can be implemented with an implanted pacemaker. Such a pacemaker is disclosed in U.S. Pat. No. 4,702,253 issued to Nappholz et al. on Oct. 27, 1987. The magnitude of the change of the impedance signal corresponds to the tidal volume and the frequency of change corresponds to respiration rate. Thus, measurement of cardiac impedance can be used as one method for obtaining $V_e$ data.

In practice, cardiac impedance can be measured through assessment of the impedance present between two or more cardiac electrodes, such as the electrodes otherwise used for pacing and/or sensing in connection with a cardiac pacemaker. In particular, it has been shown that cardiac impedance can be measured by delivering constant-current excitation pulses between two "source" electrodes, such that the current is conducted through some region of cardiac tissue. The voltage differential between two "recording" electrodes can then be measured to ascertain the impedance as reflected by the voltage differential arising from the conduction of the excitation current pulses through the tissue. Such an impedance measuring technique has proven to be practicable in connection with implantable devices, such as cardiac pacemakers.

In U.S. Pat. No. 4,721,110 to Lampadius, there is described a rheographic arrangement for a cardiac pacemaker in which the base pacing rate of the pacemaker is determined, in part, by a rheographically derived respiration rate signal.

Correlation of breathing and intrathoracic pressure fluctuations with impedance of blood in the heart is also recognized in U.S. Pat. No. 4,884,576 to Alt, which describes the measurement of impedance between two electrodes. According to the Alt '576 patent, low-pass filtering of the impedance signal yields a signal from which the patient's respiratory rate can be derived, while high-pass filtering of the same signal yields a signal from which the patient's cardiac function can be observed.

There are currently several commercially-available implantable devices which employ rheographic techniques to adjust the pacing rate in response to metabolic needs. For example, the Biorate device manufactured by Biotec International, Bologna, Italy, uses a bipolar rheographic arrangement to monitor the patient's respiration rate. The Meta-MV device manufactured by Telectronics, Inc., Englewood, Colo., uses a tripolar rheographic arrangement to monitor the patient's metabolic demand for oxygenated blood. The Precept device manufactured by CPI, St. Paul, Minn., uses a tetrapolar rheographic configuration to monitor the patient's pre-ejection interval (PEI), stroke volume, and heart tissue contractility.

The Legend Plus™ pulse generator, manufactured by Medtronic, Inc., Minneapolis, Minn. and currently undergoing clinical trials in the United States, is another example of an implantable pacemaker which employs rheography in support of its activity-response function. The Legend Plus™ delivers a biphasic excitation signal between the pulse generator's canister (serving as an indifferent electrode) and a ring electrode of a transvenous pacing/sensing lead. Impedance sensing in the Legend Plus™ carried out between the lead's tip electrode and the pulse generator canister. The Legend Plus™ impedance measuring circuitry generates an impedance waveform in which both respiration and cardiac systole are reflected. This waveform is used by the pacemaker's circuitry to derive a minute ventilation value $V_e$, as defined above. The Legend Plus™ periodically assesses a patient's $V_e$, and adjusts its base pacing rate up or down in accordance with the metabolic demand reflected in the $V_e$ value. (Various aspects of the Legend Plus™ device are described in U.S. Pat. No. 5,271,395 to Wahlstrand et al. entitled "Method and Apparatus for Rate-Responsive Cardiac Pacing," which patent is hereby incorporated by reference herein in its entirety.)

Another disclosure which relates to the use of rheography in connection with an implanted device can be found in co-pending U.S. patent application Ser. No. 08/233,901 filed on Apr. 28, 1994 in the name of Wahlstrand et al. entitled "Method and Apparatus for Sensing of Cardiac Function", which proposes a method and apparatus for obtaining an impedance waveform. The Wahlstrand et al., disclosure, which relates to the use of a specialized lead for improving the quality of an impedance waveform like that utilized in the aforementioned Legend Plus™, is hereby incorporated by reference herein in its entirety.

Yet another disclosure relating to the use of rheography in connection with implantable devices can be found in co-pending U.S. patent application Ser. No. 08/277,051 filed on Jul. 19, 1994 in the name of Gianni Plicchi et al. entitled "Time-Sharing Multi-Polar Rheography".

In an effort to minimize patient problems and to prolong or extend the useful life of an implanted pacemaker, it has become common practice to provide numerous programmable parameters in order to permit the physician to select and/or periodically adjust the desired parameters or to match or optimize the pacing system to the patient's physiologic requirements. The physician may adjust the output energy settings to maximize pacemaker battery longevity while ensuring an adequate patient safety margin. Additionally, the physician may adjust the sensing threshold to ensure adequate sensing of intrinsic depolarization of cardiac tissue, while preventing oversensing of unwanted events such as myopotential interference or electromagnetic interference (EMI). Also, programmable parameters are typically required to enable and to optimize a pacemaker rate response function as described above. Among the pacemakers manufactured by the assignee of the present invention are those that are multiprogrammable and rate-responsive, having numerous programmable parameters, including pacing mode, sensitivity, refractory period, pulse amplitude, pulse width, lower and upper rate limits, rate response gain, and activity threshold.

Those of ordinary skill in the art will appreciate that whether or not a pacemaker operates in a rate-responsive mode, the energy of stimulating pulses it delivers, i.e., the strength (amplitude) and duration (pulse width) of stimulation signals, must be of sufficient magnitude to achieve capture. (As used herein, the term "capture" will be used to refer to the occurrence of a cardiac contraction in direct response to the application of an electrical stimulation signal; to achieve capture is to evoke a cardiac response to delivery of a stimulation signal.) It is imperative that capture be maintained in order to prevent serious complications or even death, especially for those patient's who are partially or wholly dependent upon their pacemakers. At the same time, however, it is desirable for pacemaker stimulation signal energy levels to not be unnecessarily high, as this tends to decrease the useful life of the implanted device due to battery depletion, and can also have undesirable physiological side effects. In recognition of this trade-off between maintaining capture and maximizing device longevity, it has been common practice in the prior art to first determine the minimum energy level necessary to achieve capture in a patient (the patient's "pacing threshold"), and then to pace a patient's heart with pulses having an energy level that is a predetermined safety margin greater than the patient's pacing threshold.

Chief among the problems of ensuring that the safety margin between the energy level of stimulation pulses and a patient's pacing threshold is that stimulation thresholds necessary for maintaining capture often fluctuate in the short term, and can gradually change over the long term. It has been clinically observed that a lower threshold is typically exhibited immediately after implantation of the pacemaker (the so-called "acute threshold"). Inflammation in the tissue around the stimulating electrode generally drives the pacing threshold up sharply to its "peak threshold" level during the first two to six weeks after implant. Over the long term, some of this inflammation reduces, lowering the threshold from its peak to a "chronic threshold" level. The chronic threshold may not reduce to the acute level, however, since some permanent fibrous tissue will develop around the stimulating site, so that greater energy is required than for non-fibrous acute tissue.

In the short term, thresholds may decrease with exercise, for example, and may increase with other activities, including sleep.

Since patient's pacing thresholds vary over time, periodic assessments of a patient's threshold must be made, so that the energy level of stimulation pulses can be adjusted accordingly. One early proposal relating to the assessment of stimulating thresholds and adjusting stimulating levels in response to detected threshold levels can be found in U.S. Pat. No. 3,920,024 to Bowers, entitled "Threshold Tracking System and Method for Stimulating a Physiological System."

Another prior art arrangement for assessing stimulating thresholds is disclosed in U.S. Pat. No. 4,250,884 to Hartlaub et al., entitled "Apparatus For and Method Of Programming the Minimum Energy Threshold for Pacing Pulses to be Applied to a Patient's Heart." The Hartlaub et al. '884 patent is assigned to the assignee of the present invention and is hereby incorporated by reference herein in its entirety.

According to the Hartlaub '884 patent, a pacemaker and programmer are operable to function in a so-called "autothreshold" mode, wherein the pacemaker delivers a series of progressively lower energy level stimulation pulses to the patient's heart. While the pacemaker and programmer are operating in the autothreshold mode, the physician or clinician who initiated the autothreshold function monitors the patient's EKG on a strip-chart or display screen. The physician or clinician takes note of which pulse among the sequence first fails to achieve capture, and in response immediately discontinues the autothreshold test. This identifies to the programmer that the patient's pacing threshold lies between the energy levels of the two most recently delivered pulse, and the programmer can then adjust the level of pacing pulse energy to be at a level which includes at least a predetermined safety margin above the patient's threshold.

Although the method and apparatus disclosed in the Hartlaub '884 reference provides a means for determining a patient's pacing threshold so that battery depletion is minimized and patient safety is ensured, the Hartlaub '884 system requires the presence of a trained physician or clinician to perform the autothreshold procedure, and the autothreshold adjustment must be carried out in a clinical setting. This can be inconvenient and expensive for the patient. To address these issues, attempts have been made in the prior art to provide implantable pulse generators with a more fully automatic threshold detection feature, so that capture can be maintained without the need for clinical or patient intervention. Such IPGs typically rely upon electrical sensors similar to pacing leads to sense the presence of capture in response to the delivery of stimulation signals. However, the function and accuracy of these sensors have been shown to be adversely affected by one or more factors, including (but not limited to): myopotentials (electrical signals which are the product of muscle movement), electromagnetic interference (EMI), problems with sensor sensitivity (either too sensitive or not sensitive enough), and variations in the sense electrical signals as a function of changes in thoracic pressure (for example, due to changes in respiration rate, coughing, or sneezing).

Another difficulty with reliance upon electrical sensing to detect the presence or absence of capture without the necessity of physician intervention is that the sensing circuitry typically is not capable of discriminating between an intrinsic beat which would have occurred even if no stimulation pulse had been delivered, and an actual captured beat.

The above-mentioned and other difficulties associated with automating the procedure for determining a patient's pacing threshold and adjusting the stimulation pulse energy level can be generally described as involving either lack of sensitivity or lack of specificity in capture detection. (As used herein, "sensitivity" in capture detection is used to refer to the ability to avoid false negative capture detection—not recognizing when capture actually occurs—quantified as the number of loss-of-capture beats identified as such divided by the actual number of loss-of-capture beats, over a given time. On the other hand, "specificity" in capture detection refers to the ability avoid false positive capture detection—indicating that capture has occurred when it actually has not—quantified as the number of capture beats identified as such divided by the actual number of capture beats, over a given time.)

SUMMARY OF THE INVENTION

In view of the foregoing considerations, therefore, it is believed that it would be desirable to provide a cardiac pacemaker with the capability of more accurately and reliably detecting capture of the heart, i.e., of providing a pacemaker capable of detecting, with high degrees of sensitivity and specificity, loss of capture.

In accordance with one aspect of the present invention, a cardiac pacemaker uses cardiac impedance or another measurable physiological characteristic to determine whether cardiac capture is achieved following delivery of cardiac stimulation pulses. In this regard, the present invention can advantageously utilizes techniques and concepts of impedance, pressure, or oxygen saturation measurement that have heretofore been employed in connection with rate-response operation in cardiac pacemakers. In some cases, circuitry in an implantable device can advantageously be used for the dual purposes of supporting both rate-response function and threshold tracking capabilities.

In an exemplary embodiment of the invention, cardiac impedance is monitored, and peak-to-peak deflections in the cardiac impedance signal are analyzed in order to detect, with high sensitivity and specificity, loss of capture. In accordance with one feature of the present invention, enhanced capture detection is provided through utilization of a redundancy scheme wherein both cardiac impedance (or, alternatively, pressure- or oxygen saturation sensing) and sensed ventricular and/or atrial contractions are used in discriminating between capture and loss-of-capture. This enhanced capture detection is accomplished first by examining, over one or more respiratory cycles, a series of capture beats in order to establish a baseline for impedance signals. This baseline is subsequently utilized to determine whether stimulation signal thresholds are sufficient to maintain capture for succeeding heart contractions.

In accordance with one aspect of the present invention, test stimulation pulses having varying energy levels—both varying pulse widths and varying amplitudes—are delivered in order to determine the patient's stimulation threshold. This advantageously enables the pacemaker to obtain information from which a strength-duration curve can be developed for the patient. This facilitates analysis of impedance data for the purposes of applying safety margin criteria thereto, so that patient safety is ensured and pacemaker longevity is maximized.

BRIEF DESCRIPTION OF THE DRAWINGS

The foregoing and other features of the present invention will be best appreciated with reference to the following detailed description of a specific embodiment of the invention, when read in conjunction with the accompanying drawings, wherein.

DETAILED DESCRIPTION OF A SPECIFIC EMBODIMENT OF THE INVENTION

Figure 1:
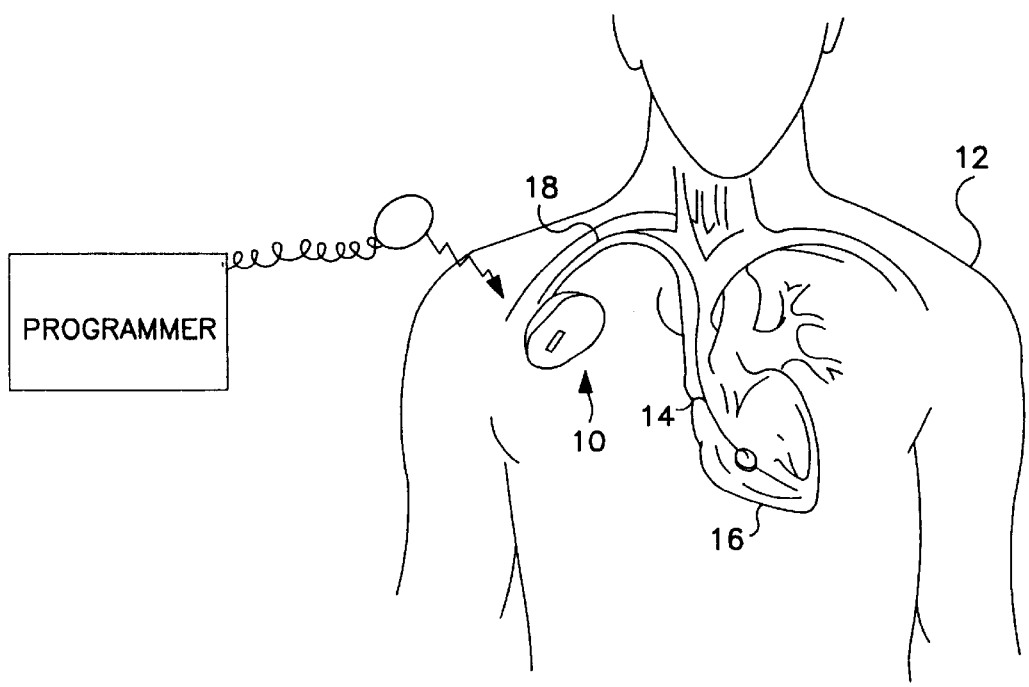
FIG. 1 is an illustration of a pacing system in accordance with one embodiment of the present invention, the pacing system including an external programming unit and body-implantable pacemaker implanted in a patient.

Referring to FIG. 1, there is shown an illustration of generally where a pacemaker 10 in accordance with one embodiment of the invention may be implanted in a patient 12. In accordance with conventional practice in the art, pacemaker 10 is housed within a hermetically sealed, biologically inert outer canister, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extends into the patient's heart 16 via a vein 18. Disposed generally near the distal end of lead 14 are one or more exposed conductive electrodes for receiving electrical cardiac signals and/or for delivering electrical pacing stimuli to heart 16. As will be appreciated by those of ordinary skill in the art, lead 14 may be implanted with its distal end situated in either the atrium or ventricle of heart 16.

Figure 2:
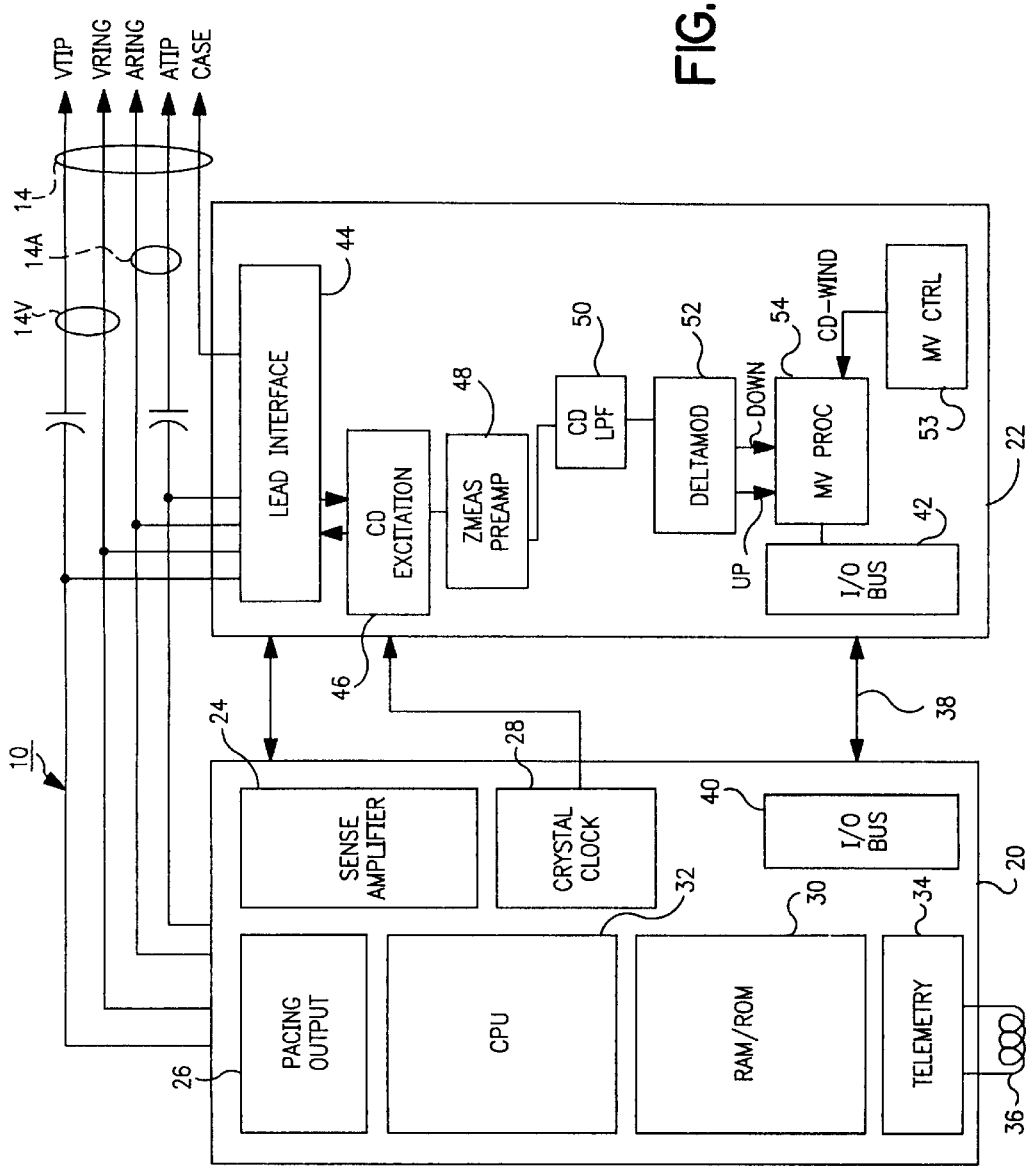
FIG. 2 is a block diagram of circuitry included within the pacemaker of FIG. 1.

Turning now to FIG. 2, there is shown a block diagram of the electronic circuitry which makes up pacemaker 10 in accordance with the presently disclosed embodiment of the invention. As can be seen from FIG. 2, pacemaker 10 comprises a primary pacing/control circuit 20 and an autocapture circuit 22. Much of the circuitry associated with pacing control circuit 20 is of conventional design, in accordance, for example, with what is disclosed in U.S. Pat. No. 5,052,388 to Sivula et al, entitled "Method and Apparatus for Implementing Activity Sensing in a Pulse Generator." The Sivula et al. '388 patent is hereby incorporated by reference herein in its entirety. To the extent that certain components of pacemaker 10 are purely conventional in their design and operation, such components will not be described herein in detail, as it is believed that design and implementation of such components would be a matter of routine to those of ordinary skill in the art. For example, pacing/control circuit 20 in FIG. 2 includes sense amplifier circuitry 24, pacing output circuitry 26, a crystal clock 28, a random-access memory and read-only memory (RAM/ROM) unit 30, a central processing unit (CPU) 32, and a telemetry circuit 34, all of which are well-known in the art.

Pacemaker 10 preferably includes internal telemetry circuit 34 so that it is capable of being programmed by means of external programmer/control unit 17 (shown in FIG. 1). Programmers and telemetry systems suitable for use in the practice of the present invention have been well known for many years.

Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Model 9760 and Model 9790 Programmers, commercially-available from Medtronic, Inc., Minneapolis, Minn. Various telemetry systems for providing the necessary communications channels between an external programming unit and an implanted device have been developed and are well-known in the art. Telemetry systems believed to be suitable for the purposes of practicing the present invention are disclosed, for example, in the following U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

Typically, telemetry systems such as those described in the above-referenced patents are employed in conjunction with an external programming/processing unit. One programmer for non-invasively programming a cardiac pacemaker is described in the above-referenced Hartlaub et al. '884 patent.

Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modelled as an air-core coupled transformer. An example of such a telemetry system is shown in the above-referenced Thompson et al. '063 patent.

In order to communicate digital data using RF telemetry, a digital encoding scheme such as is described in the above-reference Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encodes a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen position data frame may be defined, wherein a pulse in one of the time slots represents a unique four bit portion of data.

As depicted in FIG. 1, programming units such as the above-described Medtronic Model 9760 and 9790 programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head, with an antenna 36 in implanted device 10 being used to receive downlink telemetry signals and transmit uplink telemetry signals.

With continued reference to FIG. 2, pacemaker 10 is coupled to leads 14 which, when implanted, extend transvenously between the implant site of pacemaker 10 and the patient's heart 16, as previously noted with reference to FIG. 1. For the sake of clarity, the connections between leads 14 and the various components of pacemaker 10 are not shown in FIG. 2, although it will be clear to those of ordinary skill in the art that, for example, leads 14 will necessarily be coupled, either directly or indirectly, to sense amplifier circuitry 24 and pacing output circuit 26, in accordance with common practice, such that cardiac electrical signals may be conveyed to sensing circuitry 24, and pacing pulses may be delivered to cardiac tissue, via leads 14.

In the presently disclosed embodiment, two leads are employed—an atrial lead 14A having atrial tip and ring electrodes (ATIP and ARING in FIG. 2), and a ventricular lead 14V having ventricular tip and ring electrodes (VTIP and VRING in FIG. 2). In addition, as noted above, the conductive hermetic canister of pacemaker 10 serves as an indifferent electrode (CASE in FIG. 2).

As previously noted, pace/control circuit 20 includes central processing unit 32 which may be an off-the-shelf programmable microprocessor or microcontroller, but in the presently preferred embodiment of the invention is a custom integrated circuit. Although specific connections between CPU 32 and other components of pace/control circuit 20 are not shown in FIG. 2, it will be apparent to those of ordinary skill in the art that CPU 32 functions to control the timed operation of pacing output circuit 26 and sense amplifier circuit 24 under control of programming stored in RAM/ROM unit 30. It is believed that those of ordinary skill in the art will be familiar with such an operative arrangement.

With continued reference to FIG. 2, crystal oscillator circuit 28, in the presently preferred embodiment, a 32,768-Hz crystal controlled oscillator, provides main timing clock signals to pace/control circuit 20 and to autocapture circuit 22.

It is to be understood that the various components of pacemaker 10 depicted in FIG. 2 are powered by means of a battery (not shown) which is contained within the housing pacemaker 10 in accordance with common practice in the art. For the sake of clarity in the Figures, the battery and the connections between it and the other components of pacemaker 10 are not shown.

Pacing output circuit 26, which functions to generate pacing stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits which would be suitable for the purposes of practicing the present invention.

As shown in FIG. 2, pace/control circuit 20 is coupled to capture detect circuit 22 by means of multiple signal lines, designated collectively as 38 in FIG. 2. An I/O interface 40 in pace/control circuit 20, and a corresponding I/O interface 42 in capture detect circuit 22, coordinate the transmission of signals between between the two units.

Capture detect circuit 22 includes a lead interface circuit 44 which is essentially a multiplexer that functions to selectively couple and decouple capture detect circuit 22 to the VTIP, VRING, ATIP, ARING, and CASE electrodes, as will be hereinafter described in greater detail.

Coupled to lead interface circuit 44 is a capture detect excitation (CD EXCITATION) circuit 46 which functions to deliver biphasic constant-current pulses between various combinations of lead electrodes (VTIP, VRING, etc. . . .) for the purpose of measuring cardiac impedance. In particular, CD EXCITATION circuit 46 delivers biphasic excitation pulses of the type delivered by the above-noted Legend Plus™ device, and in accordance with the method and apparatus described in the above-referenced Wahlstrand et al. '395 patent. The electrodes between which the excitation pulses are delivered will vary depending upon whether atrial or ventricular capture thresholds are being evaluated. The selection of the electrodes is made by lead interface circuit 44, under control of signals asserted by pace/control circuit 20 and conveyed to capture detect circuit 22 over bus 38. For ventricular capture threshold evaluation, for example, biphasic pulses may be delivered at a rate of 128-Hz between the ventricular ring electrode VRING and the pacemaker canister CASE. Similarly, for atrial capture threshold determination, the pulses may be delivered between the atrial ring electrode ARING and CASE.

To measure cardiac impedance, capture detect circuit 22 monitors the voltage differential present between pairs of electrodes as excitation pulses are being injected as described above. Again, the electrodes from which voltage differentials are monitored will vary depending upon whether atrial or ventricular thresholds are being assessed. In one embodiment of the invention, the same electrodes (i.e., VRING and CASE for ventricular, ARING and CASE for atrial) are used for both delivery of excitation pulses and voltage differential monitoring. It is contemplated, however, that the electrode combinations for excitation and measurement may be among the programmable settings which may be altered post-implant with the programming system.

An impedance measurement preamplifier circuit ZMEAS PREAMP 48 is coupled to the voltage differential measurement electrodes during delivery of the excitation pulses. ZMEAS PREAMP circuit 48 comprises three stages. The first is a low-noise amplifier (with a gain of 20 in the presently preferred embodiment) which also performs a high-pass filtering function. The second stage is a gain amplifier (with a gain of 8 in the presently preferred embodiment). The final stage is a 128-Hz sample-and-hold circuit. As noted above, biphasic excitation pulses are delivered at a rate of 128-Hz; accordingly, 128 voltage differential measurements are made each second. The sample-and-hold stage of ZMEAS PREAMP circuit 48 holds each of these voltages for presentation to remaining circuitry in capture detect circuit 22.

It is believed that the design and implementation of the preamplifier, gain, and sample-and-hold stages of ZMEAS PREAMP circuit 48 would be a matter of routine engineering to those of ordinary skill in the circuit art. Accordingly, the details of the design of ZMEAS PREAMP circuit 48 will not be described herein.

With continued reference to FIG. 2, the sampled output voltages from ZMEAS PREAMP circuit 48 are presented to a capture detect low-pass filter circuit CD LPF 50, which in the presently preferred embodiment of the invention is a single-pole low-pass filter with a pole at 6.4-Hz, to bandlimit noise in the sampled impedance waveform. Again, it is believed that the design and implementation of CD LPF circuit 50 would be a matter of routine engineering to those of ordinary skill in the art. The output from CD LPF circuit 50 is a voltage waveform whose level at any given time is directly proportional to cardiac impedance measured between the selected electrodes. Thus, the CD LPF output signal will be referred to herein as an impedance waveform.

After low pass filtering in CD LPF circuit 50, the impedance waveform is provided to a delta modulator circuit DELTAMOD 52, which performs an analog-to-digital conversion (ADC) function. DELTAMOD circuit 52 has two digital output signals, designated in FIG. 2 as UP and DOWN. DELTAMOD circuit 52 operates at a rate of 2-kHz, meaning that following each of two thousand modulator cycles per second, it either asserts its UP output, asserts its DOWN output, or asserts neither output. As will be appreciated by those of ordinary skill in the art, DELTAMOD 52 asserts its UP output whenever the output voltage (impedance waveform) from CD LPF circuit 50 has risen by a predetermined incremental amount since the last DELTAMOD cycle, and asserts its DOWN output whenever the impedance waveform from CD LPF circuit 50 has fallen by a predetermined incremental amount since the previous DELTAMOD cycle. In the presently preferred embodiment, DELTAMOD circuit 52 has a resolution of 0.1-Ω for atrial capture threshold evaluation, and 0.25-Ω for ventricular capture threshold evaluation. That is, for atrial capture threshold evaluation, the UP or DOWN signals are asserted each DELTAMOD cycle if the impedance waveform rises or falls by an amount corresponding to a 0.1-Ω change in cardiac impedance; similarly, for ventricular capture threshold evaluation, the UP or DOWN signals are asserted each DELTAMOD cycle if the impedance waveform rises or falls by an amount corresponding to a 0.25-Ω change in cardiac impedance.

Figure 3:
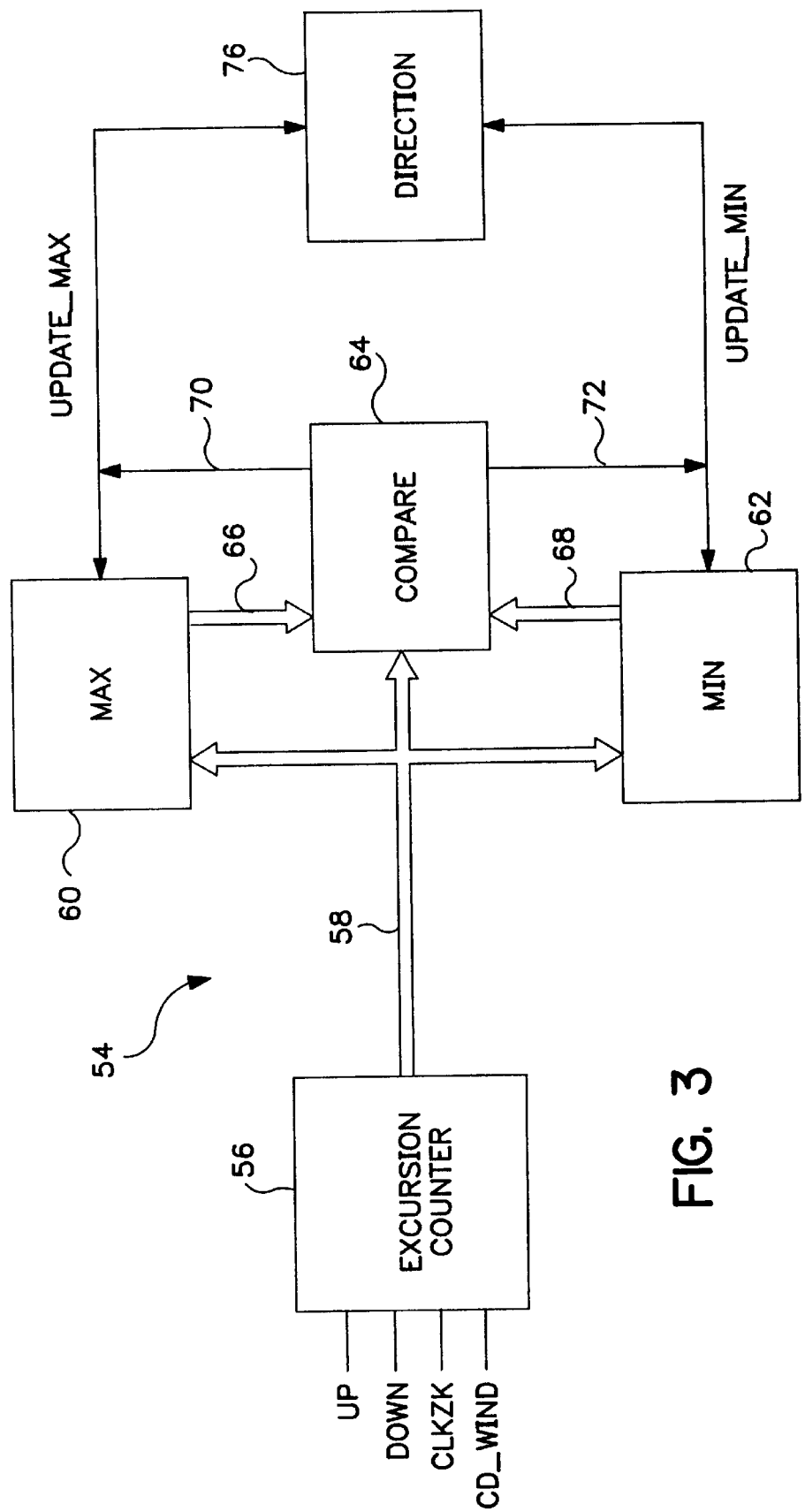
FIG. 3 is a block diagram of a logic processing circuit from the block diagram of FIG. 2.

The UP and DOWN output signals from DELTAMOD circuit 52 are applied to a processing circuit MV PROC 54, which is shown in block diagram form in FIG. 3. As shown in FIG. 3, the UP and DOWN output signals from DELTAMOD circuit 52 are applied to an excursion counter 56 in MV PROC 54. A 2-kHz clock signal, which may be derived from crystal clock circuit 28 in pace/control circuit 20, is also applied to excursion counter 56, along with a signal identified as CD_WIND, which defines a capture detect window following the delivery of each biphasic excitation pulse, as will be hereinafter described in greater detail. As shown in FIG. 2, the CD_WIND signal is generated by an MV CTRL circuit 53 and applied to MV PROC circuit 54 to inform MV PROC circuit 54 when a capture detect window is occurring. At the conclusion of each capture detect window, MV CTRL circuit 53 asserts an interrupt signal CD_INT, which signal is among those communicated to pace/control circuit 20 via lines 38. Specifically, the CD_INT interrupt signal is applied to CPU 32 as an interrupt signal thereto.

Excursion counter 56 is a conventional binary up/down counter that is activated upon assertion of the CD_WIND signal. While activated, excursion counter 56 increments or decrements its binary digital output count value on each cycle of the 2-kHz clock input signal. Whether counter 56 increments or decrements its value on a given clock cycle depends upon whether the UP or DOWN signal is asserted during that cycle. The binary output count value from excursion counter 56 is applied, on multiple-bit line 58, to the inputs of a multiple-bit MAX register 60 and a multiple-bit MIN register 62, as well as to a compare circuit 64. MAX register 60 and MIN register 62 function to store the maximum and minimum binary digital output values, respectively, that are attained by excursion counter 56 during a capture detect window. These maximum and minimum values are applied, on lines 66 and 68, respectively, to comparator 64.

MV PROC circuit operates as follows: prior to assertion of the CD_WIND signal, MAX register 60 and MIN register 62 are reset to store a zero value. Similarly, the starting count value of excursion counter 56 is reset to zero.

When CD_WIND is asserted, signalling the beginning of a capture detect window, excursion counter 56 will begin to increment or decrement its output value at a rate of 2-kHz; that is, two thousand times per second, the value of excursion counter will be updated—either incremented, decremented, or staying unchanged—depending upon the logic state of the UP and DOWN input signals. Assuming that the UP and DOWN signals are each asserted some number of times during a capture detect window, this will cause the output value from excursion counter 56 to fluctuate up and down over the course of that capture detect window. As this occurs, the output value from counter 56 is constantly being applied to compare circuit 64, which is also supplied with the current MAX and MIN values (on lines 66 and 68). Whenever compare circuit 64 detects an excursion counter output value, on line 58, which exceeds the value currently stored in MAX register 60, compare circuit 64 asserts an output signal UPDATE_MAX on line 70, which is applied to MAX register 60. Upon assertion of UPDATE_MAX, MAX register 60 replaces its currently stored value with the new maximum value present on line 58.

Similarly, during a capture detect window, when compare circuit 64 detects an excursion counter output value on line 58 which is less than the value currently stored in MIN register 62, compare circuit 64 asserts an UPDATE_MIN signal on line 72, which is applied to MIN register 62. Upon assertion of the UPDATE_MIN signal, MIN register 62 replaces its currently stored value with the new minimum value then present on lines 58.

With continued reference to FIG. 3, MV PROC circuit 54 further includes a DIRECTION circuit 76, which functions to maintain a one-bit value indicative of the direction of excursions made by the excursion counter during a capture detect window. DIRECTION circuit 76 receives the UPDATE_MAX and UPDATE_MIN values on lines 70 and 72, respectively. DIRECTION circuit stores a binary "one" if MAX register 60 was updated after MIN register 62 during a capture detect window (indicating a positive excursion in the impedance waveform), and stores a binary "zero" if MIN register 62 was updated after MAX register 60 (indicating a negative excursion in the impedance waveform).

Those of ordinary skill in the art will appreciate, based upon the foregoing description, that MV PROC circuit 54 operates such that upon termination of a given capture detect window, signalled by the deassertion of the CD_WIND signal, and assertion of the CD_INT interrupt signal, the values stored in the MAX and MIN registers 60 and 62 will represent the maximum and minimum output values, respectively, attained by excursion counter 56 during the window, and that the DIRECTION value reflects whether the excursion counter was undergoing a positive or negative excursion during the capture detect window. Those of ordinary skill in the art will further appreciate that since the UP and DOWN signals are asserted by DELTAMOD circuit 52 in response to positive and negative excursions, respectively, in the impedance waveform provided from CD LPF circuit 50, the MAX and MIN values at the end of a capture detect window reflect the maximum and minimum values of the impedance waveform during that window. In particular, the MAX and MIN values will be binary digital values that are directly proportional to the maximum and minimum cardiac impedances, respectively, present in the cardiac chamber being analyzed during a capture detect window. When CPU 32 receives the CD_INT interrupt signal, it is alerted that the MAX and MIN registers in MV PROC circuit 54 may be read, i.e., that the MAX and MIN values are valid. CPU 32 may then use these maximum and minimum values (along with the DIRECTION value from DIRECTION circuit 76) to assess whether cardiac capture has been achieved, as will be hereinafter described in greater detail.

In general, pacemaker 10 in accordance with the presently disclosed embodiment of the invention is operable periodically to determine what minimum stimulation pulse energy level is required to achieve capture in a patient's heart, and to thereafter adjust the level of stimulation pulse energy levels to a level which includes a predetermined safety margin above the minimum level so determined. It is contemplated that operation of pacemaker 10 to perform these functions can be manually initiated through transmission of appropriate programming command signals from an external programming/control unit.

Pacemaker 10 assesses a patient's pacing threshold by monitoring cardiac impedance following delivery of a pacing pulse, to ascertain whether capture has been achieved by that pulse. By varying the energy level of the pulses, pacemaker 10 can determine when a particular pulse has insufficient energy to capture the heart, i.e., has an energy level below the patient's pacing threshold.

Evaluation of cardiac impedance is performed by delivering a series of biphasic excitation pulses to the cardiac tissue during the above-noted capture detect window which occurs at a predetermined time after delivery of pacing pulses during the capture detect assessment. As previously noted, this capture detect window is defined by assertion of one or more signals, including the CD_WIND signal, by CPU 32 in pace/control circuit 20. In a presently preferred embodiment of the invention, the starting and ending times for the capture detect window, which are expressed relative to the delivery of a stimulation pulse, are among the programmable parameter values which can be selected or altered by a physician or clinician using the pacemaker programmer. In particular, the capture detect window start time can be programmed to begin between (approximately) 8- and 250-mSec after the delivery of a stimulation pulse, and can have a duration of between (approximately) 8- and 500-mSec for atrial capture detection and between (approximately) 8- and 500-mSec for ventricular capture detection. In one embodiment, the capture detect window is defined as beginning 50-mSec after delivery of a stimulation pulse, and lasts for 100-mSec thereafter for atrial capture detection, and lasts for 200-mSec thereafter for ventricular capture detection.

During the capture detect window, capture detect circuit 22 (and in particular, excitation circuit 46) delivers a series of biphasic excitation pulses between two electrodes, at a rate of 128-Hz. The electrodes between which the pulses are delivered are selected by lead interface circuit 44 under control of signals issued by pace/control circuit 20. The presently preferred method involves delivering the excitation pulses between VRING and CASE for ventricular impedance sensing, and between ARING and CASE for atrial impedance sensing, although the selection of particular electrode pairs for impedance sensing could also be among the programmable options of pacemaker 10.

Figure 4:
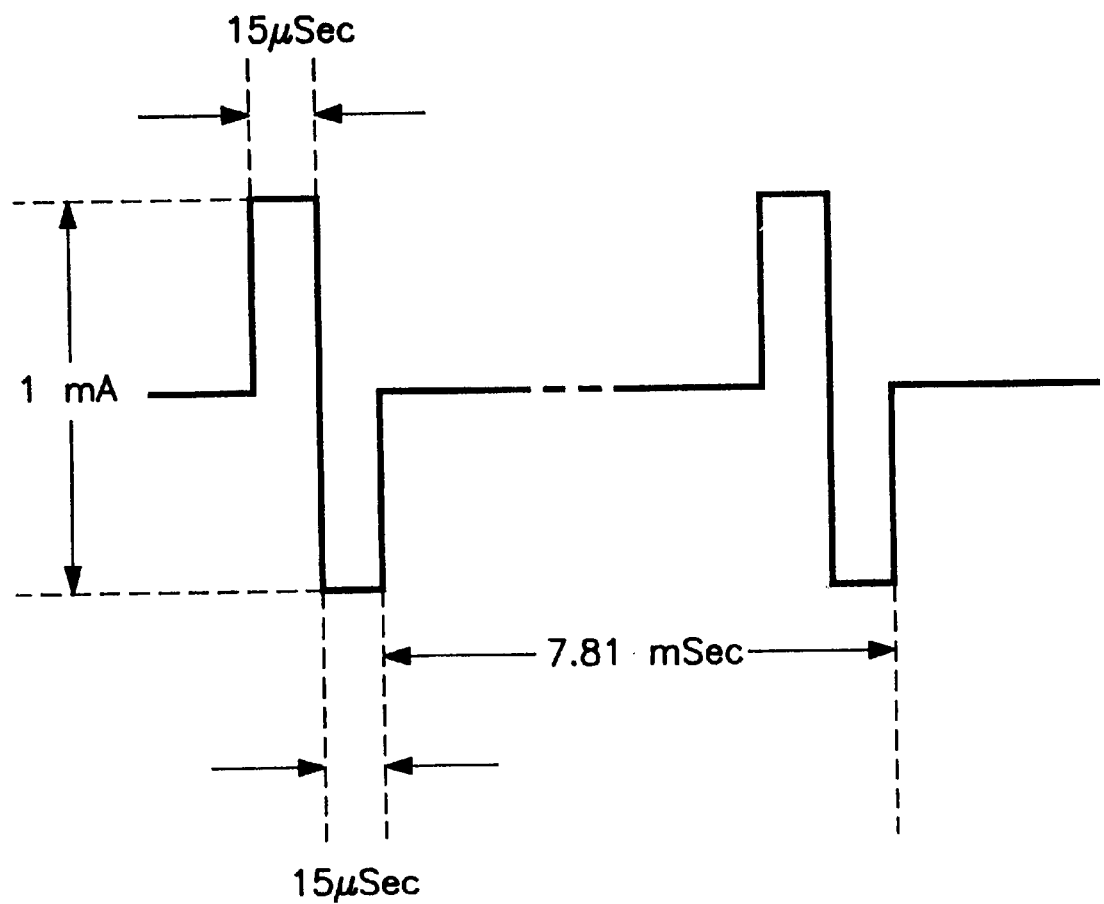
FIG. 4 is an illustration of a biphasic excitation pulse generated by the circuitry of FIG. 2.

An illustration of one excitation pulse is provided in FIG. 4. It is believed that the biphasic nature of the excitation pulses, such as the one depicted in FIG. 4, offers the advantages over a monophasic pulse that the peak amplitude of the excitation pulse is minimized given the overall energy content of the pulse, electrode polarization is canceled, and DC current is balanced to avoid long-term lead metal-ion oxidation. As shown in FIG. 4, each phase of the biphasic pulse lasts for approximately 15-$\mu$Sec, and the pulses are delivered once every 7.81-mSec (128-Hz).

While excitation circuit 46 is delivering the biphasic excitation pulses, the voltage differential between two electrodes is monitored. Once again, the selection of two electrodes between which a voltage differential is monitored is made by lead interface circuit 44 under control of CPU 32 in pace/control circuit 20. In the presently preferred embodiment, for each chamber (atrial and ventricular) the same electrodes used for excitation are also used for sensing. Thus, for the ventricular chamber, the VRING and CASE electrodes are used for excitation and sensing, while for the atrial chamber, ARING and CASE are used for excitation and sensing.

The sensed voltage differential signal (i.e., the raw impedance waveform) is processed by ZMEAS PREAMP circuit 48, CP LPF circuit 50, DELTAMOD circuit 52, and MV PROC circuit 54 as described above, in order to derive MAX, MIN, and DIRECTION values, as also described above. During a given capture detect window (either atrial or ventricular), these values are presented to pace/control circuit 20 via bus 38, for storage in RAM/ROM unit 30 and subsequent processing according to a capture detect algorithm to be hereinafter described in greater detail.

Figure 5A:
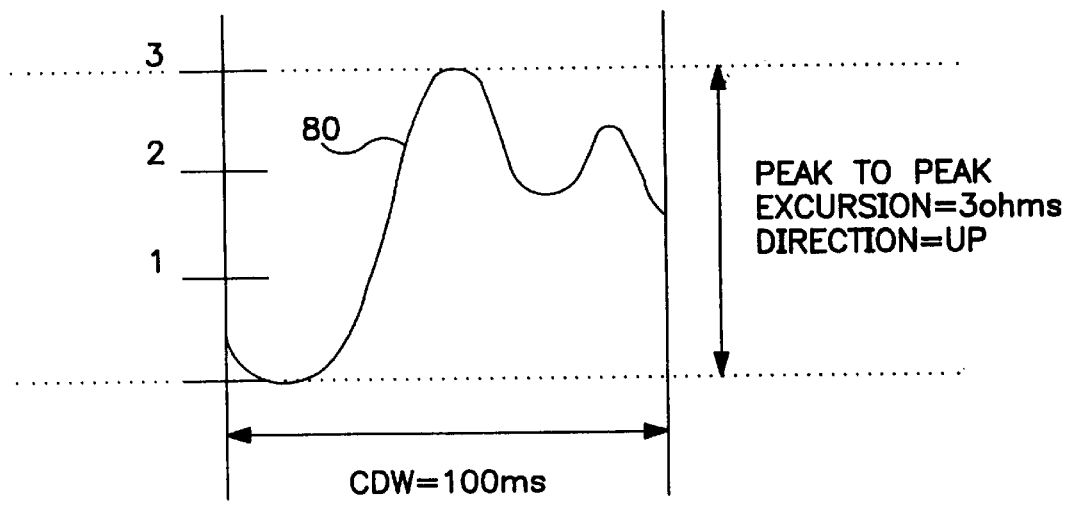
FIGS. 5a and 5b are illustrations of cardiac impedance waveforms processed by the circuitry of FIG. 2.

The MAX, MIN, and DIRECTION values derived from an impedance waveform during a particular time period provide a simple and reliable means for characterizing the morphology of the waveform during that time period, and hence provide an effective basis for discriminating between signals of different morphology. This can perhaps be best appreciated with reference to FIGS. 5a and 5b, which illustrate impedance waveforms during a 100-mSec window. Impedance waveform 80 in FIG. 5a is shown to undergo a maximum peak-to-peak excursion of 3-$\Omega$, and the magnitude of this excursion would be reflected in the MAX and MIN values generated by capture detect circuit 22 (and in particular, in the difference between the MAX and MIN values). The DIRECTION value for waveform 80 would indicate "up," since the MAX value would be updated after the MIN value during the capture detect window of FIG. 5a.

Figure 5B:
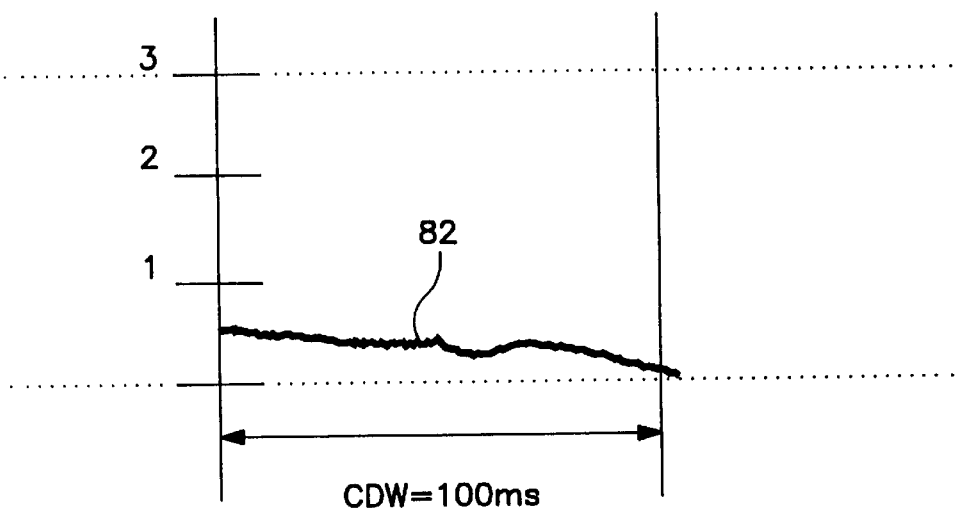

Impedance waveform 82 in FIG. 5b, on the other hand, undergoes much less of an excursion during the capture detect window, and this would be reflected in much smaller difference in MAX and MIN values derived from impedance waveform 82. Also, the DIRECTION value for waveform 82 would indicate "down," since the MIN value for waveform 82 would be updated after the MAX value during the capture detect window.

As shown from a comparison of FIGS. 5a and 5b, therefore, those of ordinary skill in the art will appreciate that capture detect circuit 22 provides a means for discriminating between signals of differing morphology. The manner in which this capability can be applied to discriminating between capture and loss-of-capture can be perhaps best understood with reference to the timing diagrams of FIGS. 6a, 6b, 6c, and 6d, and FIGS. 7a, 7b, and 7c, which each depict a portion of a patient's ECG signal in timed relation to an impedance signal monitored by the apparatus of FIGS. 2 and 3 and to an indication of the starting and stopping times of certain blanking and capture detection windows established by pacemaker 10 in response to such signals.

Figure 6A:
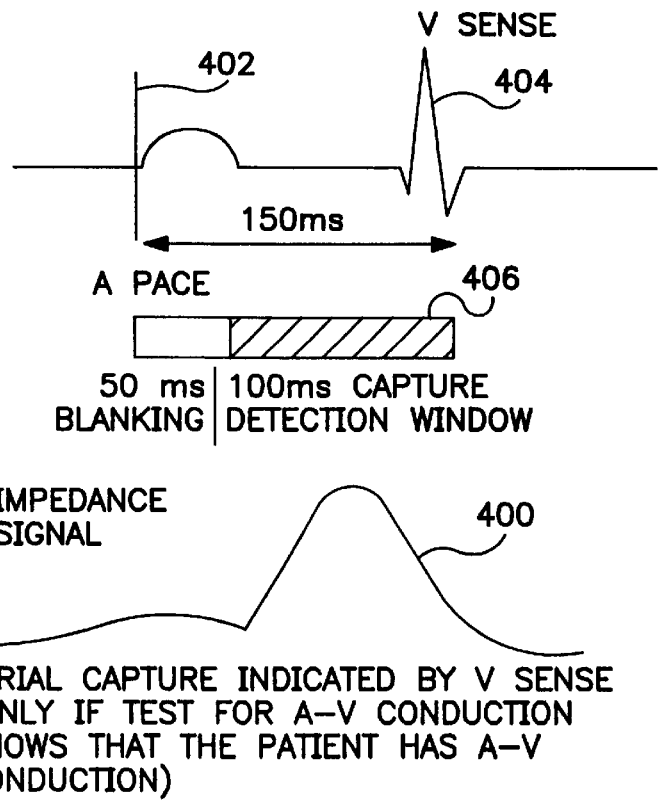
FIGS. 6a, 6b, 6c, and 6d are diagrams showing atrial cardiac impedance waveforms in timed relation to a patient's ECG signal.

In FIG. 6a, a situation is illustrated in which a sensed ventricular event 404 occurs within a capture detection window 406, following the occurrence of an atrial paced event 402. In this case, if it has been previously determined that the patient has normal A-V conduction, it becomes obvious that atrial capture is indicated by the appearance of sensed ventricular signal 404, and it is not necessary to rely upon impedance signal 400 to determine whether capture has or has not been achieved.

Figure 6B:
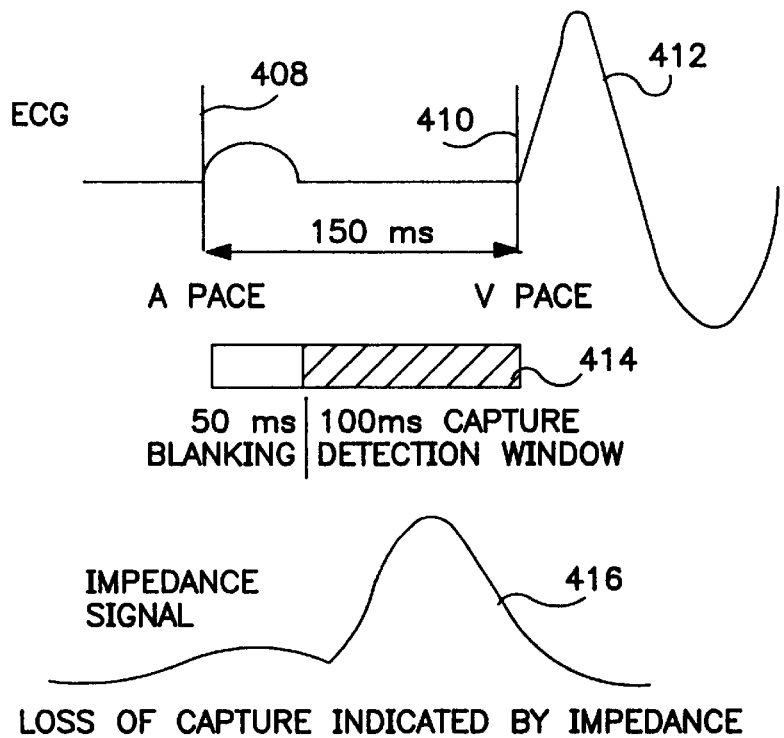

FIG. 6b illustrates a situation in which no sensed signal occurs during capture detection window 414. However, a noticeable, positive excursion of impedance signal 416 occurs during capture detection window 414, reliably indicating that atrial capture has occurred. Those of ordinary skill in the art having the benefit of the present disclosure will appreciate that if impedance signal 416 is the impedance waveform which is applied by CD LPF circuit 50 to the input of DELTAMOD circuit 52 (see FIG. 2), operation of capture detect circuit 22 as previously described will result in generation of MAX, MIN, and DIRECTION values which reflect the positive excursion of impedance signal 416 during capture detect window 414.

Figure 6C:
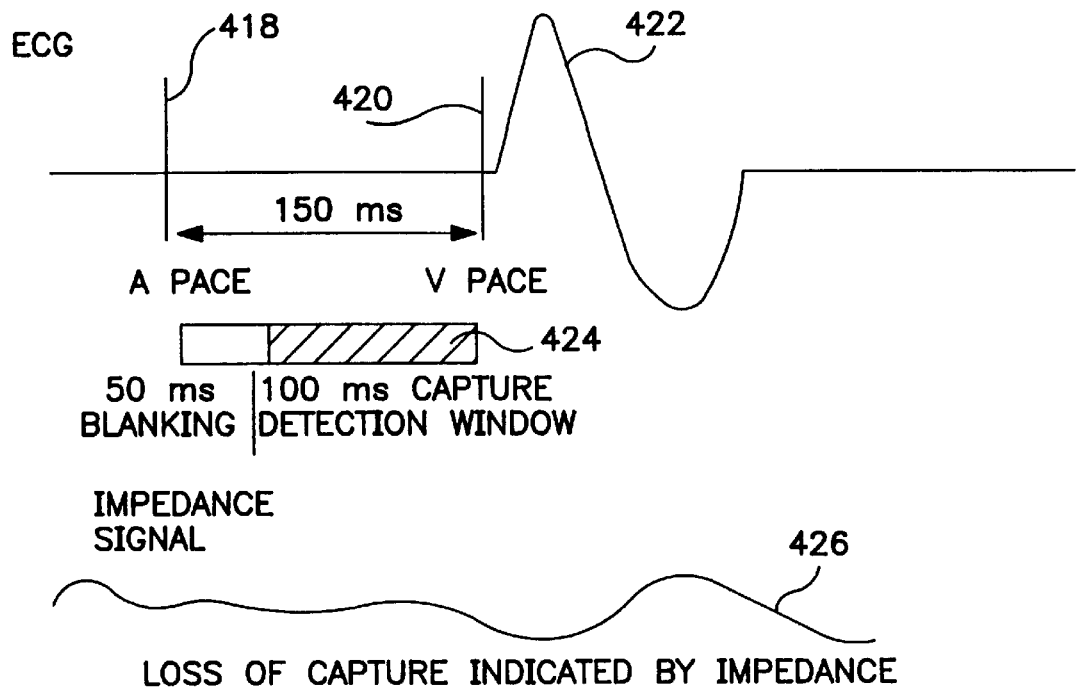

In FIG. 6c, neither a sensed signal or a noticeable excursion in impedance signal 426 is present during capture detection window 424. In this situation, a pacing device with no impedance signal available, would not know whether or not capture has been achieved as a result of atrial pace 418. This case illustrates the enhanced reliability and accuracy of detecting capture or loss-of-capture in accordance with the present invention. That is, without further examination of impedance signal 426 in this instance, there would be some doubt as to the reliability of the conclusion that loss-of-capture is indicated. However, when impedance signal 426 is obtained and processed by capture detection circuit 22, those of ordinary skill in the art would appreciate that the resultant MAX, MIN, and DIRECTION values will reflect the morphology of impedance signal 426 and will further be readily distinguishable from corresponding MAX, MIN, and DIRECTION values derived, for example, from impedance waveform 416 in FIG. 6b. Thus, capture detection circuit 22 in accordance with the presently disclosed embodiment of the invention facilitates the accurate and specific discrimination between capture and loss of capture, in that it facilitates recognition of differences in cardiac impedance waveform morphology.

Figure 6D:
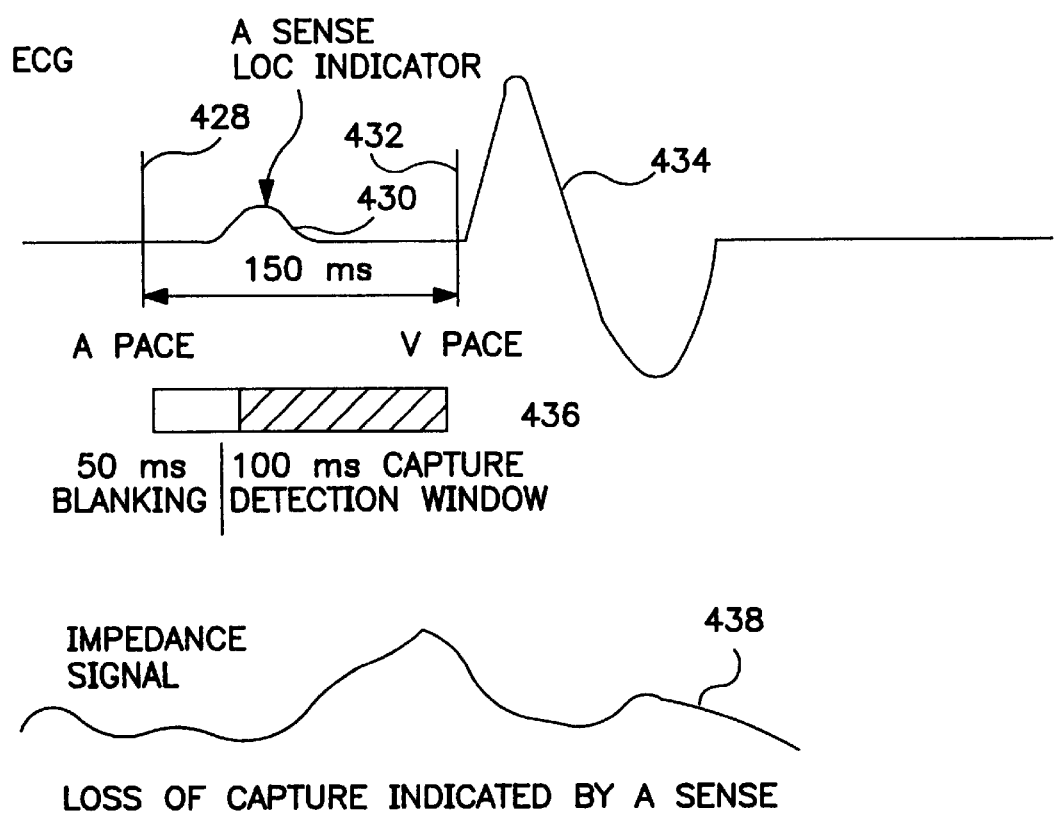

Turning now to FIG. 6d, a somewhat uncommon situation is illustrated wherein a sensed atrial event 430 occurs during capture detection window 436 following an atrial pace event 428. This is an example of when it is not necessary to examine impedance signal 438 because the occurrence of such a signal during blanking detection window 436 is a clear indication of loss of capture. Nonetheless, it is believed that it may be beneficial to have available occasionally redundant discrimination criteria to ensure sensitive and specific detection of capture and/or loss-of-capture.

Figure 7A:
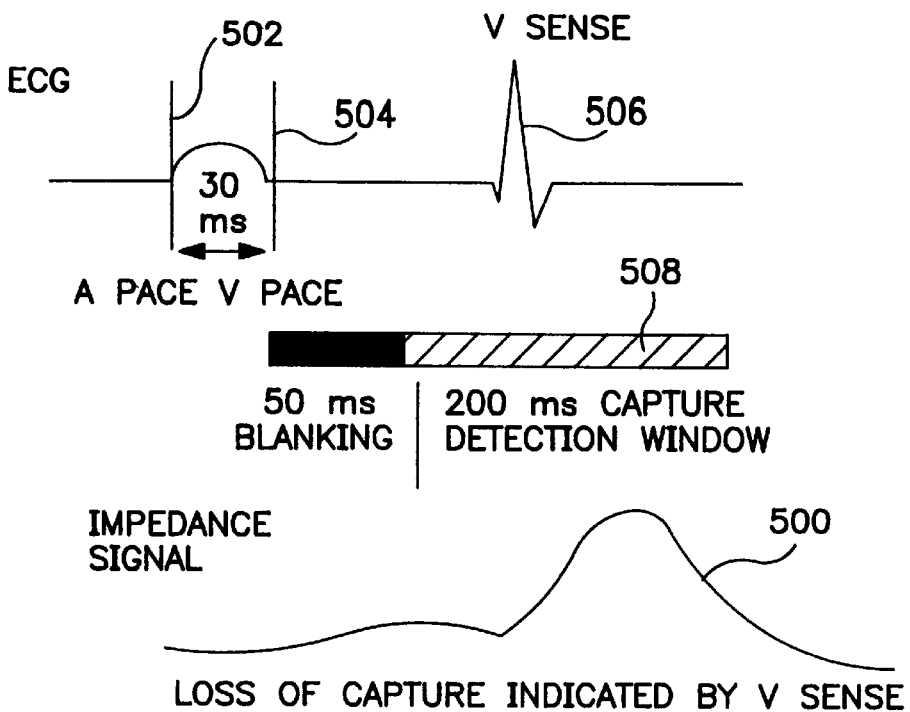
FIGS. 7a, 7b, and 7c are diagrams showing ventricular cardiac impedance waveforms in timed relation to a patient's ECG signal.
Figure 7B:
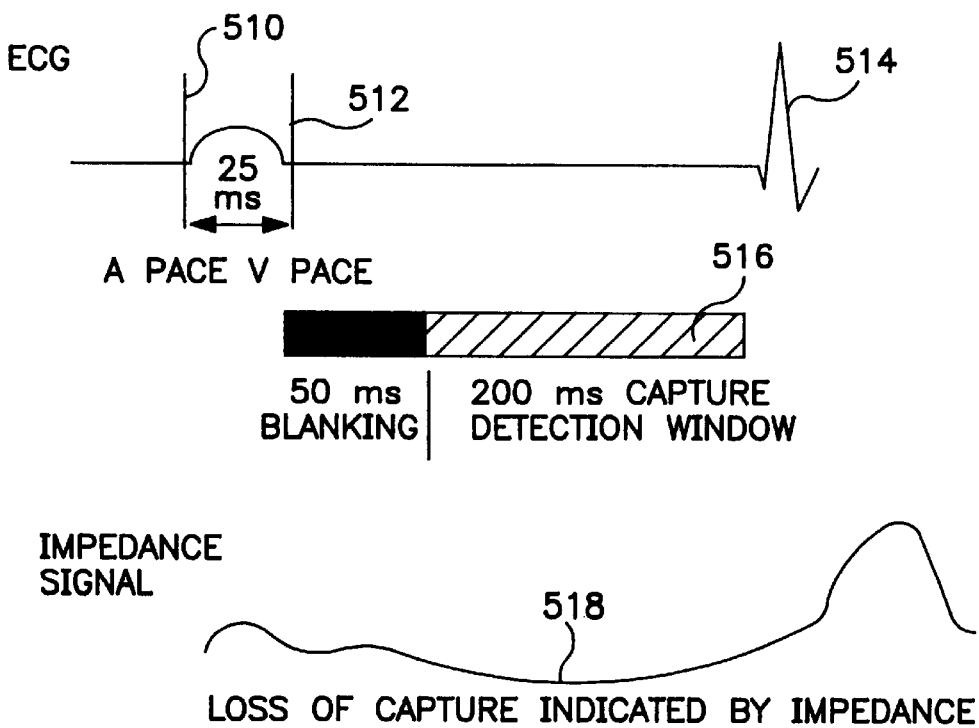
Figure 7C:
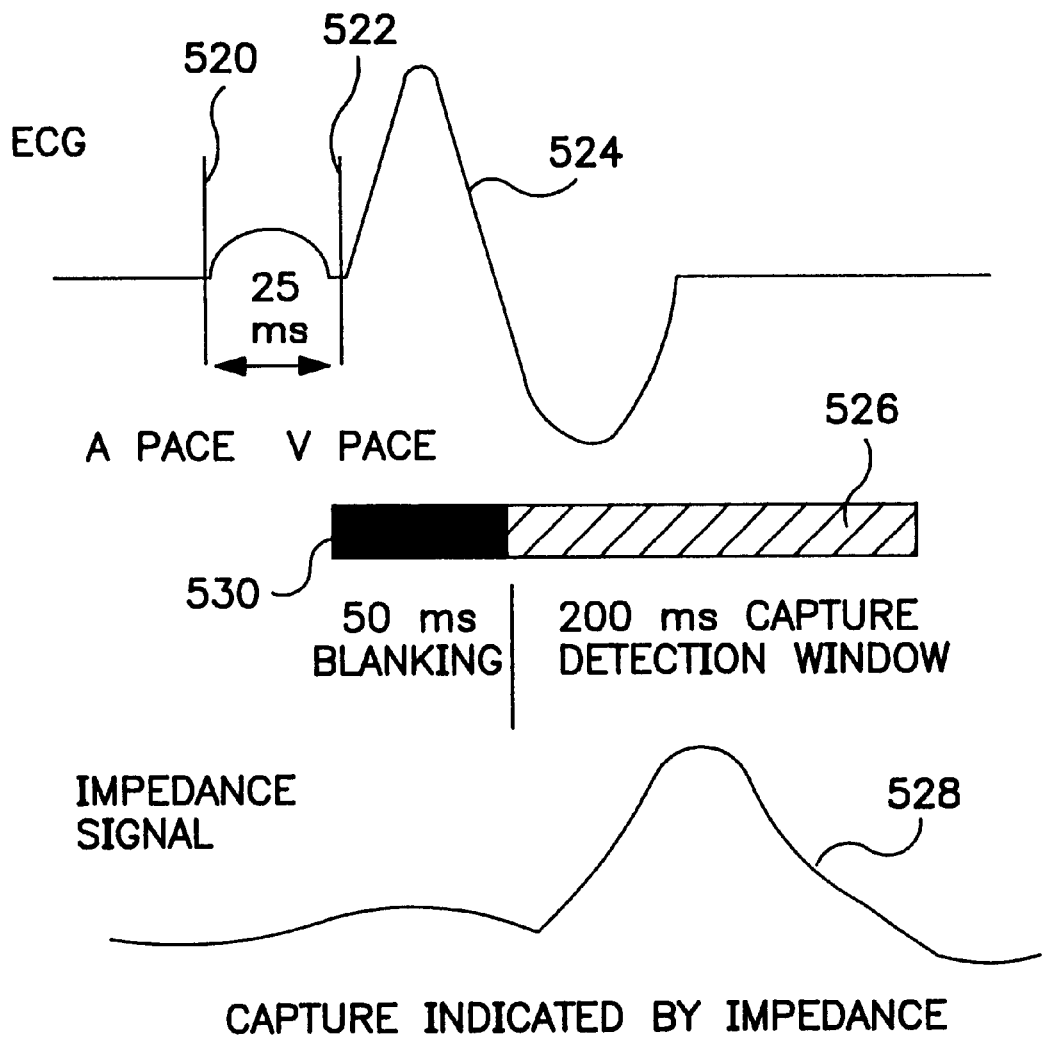

Whereas FIGS. 6a, 6b, 6c, and 6d relate to methods applicable to atrial capture detection, FIGS. 7a, 7b, and 7c illustrate methods which apply to ventricular capture detection. FIG. 7a shows a situation in which a sensed ventricular event 506 occurs during capture detection window 508 immediately following a ventricular pace 504. In this case, ventricular sense signal 506 indicates that loss-of-capture is indicated. Therefore, although a noticeable excursion of the impedance signal 500 may occur in the situation depicted in FIG. 7a, impedance signal 500 will be ignored under the guidelines in accordance with the present invention. This is yet another example of when it may not be necessary to examine the impedance signal, but where it may nonetheless be desirable to have redundancy with regard to discrimination criteria.

FIG. 7b depicts a situation in which neither a noticeable excursion in impedance signal 518 nor a sensed event occurs during capture detection window 516. In accordance with the presently disclosed embodiment of the invention, a determination of loss-of-capture in this case has a higher degree of reliability with regard to the accuracy of the result due to the redundancy provided by examination of the impedance signal.

FIG. 7c illustrates a common situation in which no sensed event occurs during detection window 526 following blanking interval 530 initiated after delivery of a ventricular pace 522. Nonetheless, it can be seen from FIG. 7c that capture has occurred. Since an evoked response occurs in FIG. 7c so close in time to the pacing stimulus, it is difficult, if not impossible, for a sense amplifier to reliably detect the response. In this case, impedance signal 528 provides critical information, enabling the device to correctly conclude that capture has been achieved. That is, the correct conclusion (that capture was achieved) is reflected by the excursion in impedance waveform 528 during detection window 526, whereas such conclusion may not be perceptable from the sense amplifier signal alone. The impedance waveform excursion would, in turn, be reflected in the MAX, MIN, and DIRECTION values derived in accordance with the presently disclosed embodiment of the invention, and such values would be readily distinguishable from corresponding values derived from, for example, impedance waveform 518 from FIG. 7b present in a loss-of-capture situation.

Figure 8:
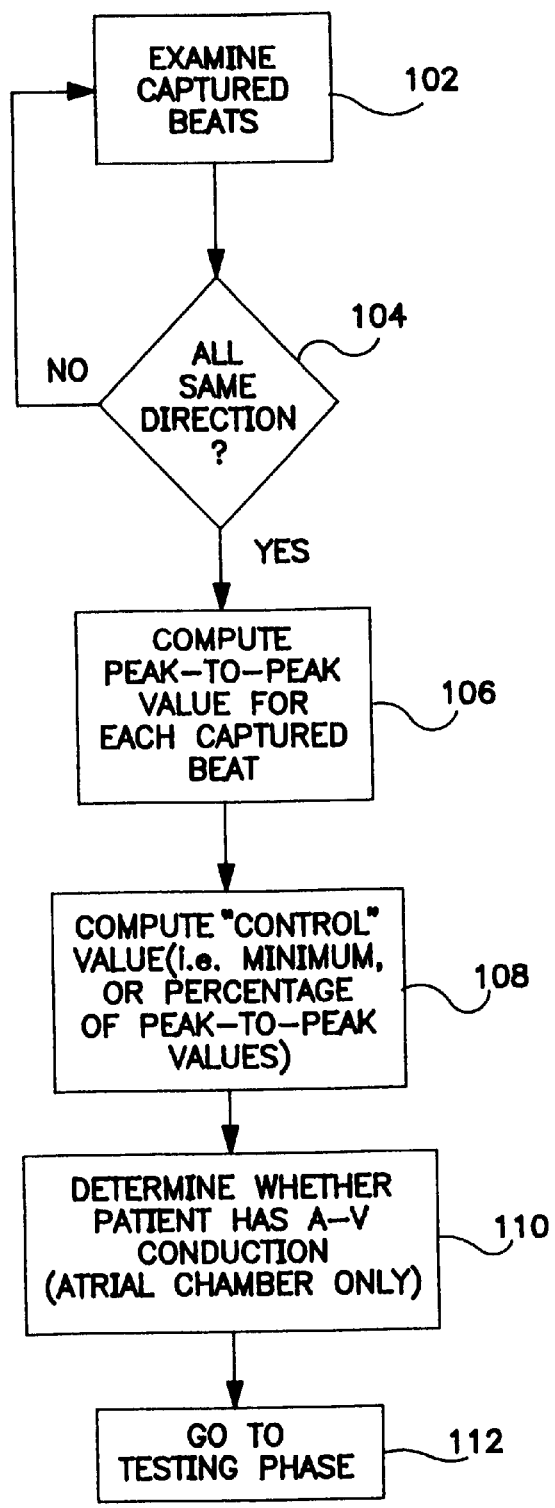
FIG. 8 is a flow diagram showing the steps involved in an initialization phase of a capture detection algorithm in accordance with the disclosed embodiment of the invention.

The method of pacing threshold determination in accordance with the presently disclosed embodiment consists of two main phases: an initialization phase, and a testing phase. FIG. 8 shows a flowchart illustrating the initialization phase for the presently preferred embodiment for achieving enhanced capture detection associated with operating pacemaker 10 illustrated in FIGS. 1 and 2. The initialization phase must be performed twice, once for each chamber (ventricular and atrial) of the heart. As will be hereinafter described, the initialization phase for each chamber is the same, with the exception of one step that is performed for the atrial chamber initialization only. For each chamber, the initialization phase begins with block 102 of the flowchart of FIG. 8, wherein a series of captured heart beats is examined to establish a baseline for impedance measurements. The examination of captured beats in step 102 is accomplished by temporarily pacing the chamber under test at a relatively rapid rate and with pacing pulses of relatively large energy levels, to ensure capture. (For example, the initialization pulses may be delivered at or near the pacemaker's maximum pulse width and amplitude settings.) A capture detect window occurs following delivery of each pacing pulse in the chamber under test during this initialization phase, during which impedance measurement is carried out as described above. Thus, a MAX, MIN, and DIRECTION value are generated for each pacing pulse delivered during this phase, and these values are stored in RAM/ROM unit 30 for subsequent processing.

Preferably, the rate at which pacing occurs during the initialization phase of the capture detect procedure is fast enough to prevent the patient from breaking through with a sinus rhythm, but slow enough to avoid the undesirable side effects of rapid stimulation (e.g., pacemaker-induced tachycardia). The following Table 1 sets forth the presently preferred test rates, in beats per minute (BPM), for performing the automatic capture detection, which vary according to the measured rate of intrinsic cardiac activity in the patient:

TABLE 1

| MEASURED INTRINSIC RATE (BPM) | TEST RATE (BPM) |
| --- | --- |
| <70 | 90 |
| ≧70 and <80 | 100 |
| ≧80 and <90 | 110 |
| ≧90 and <100 | 120 |

In the preferred embodiment, ten captured beats are examined in block 102, although the number of captured beats examined in block 102 may be more or less than this. In any case, the duration of the initial examination in block 102 is preferably sufficient to last for at least one complete respiration cycle.

After delivery of the initial examination pulses in block 102, the process proceeds to decision block 104, wherein CPU 32 determines whether all of the DIRECTION values generated in connection with the delivery of the examination pulses are the same. If not, flow returns to block 102, wherein another series of captured beats is examined.

Assuming that all of the DIRECTION values for the captured beats examined in block 102 are found to be the same in block 104, flow proceeds to block 106, wherein CPU 32 computes a peak-to-peak impedance value for each of the captured beats. As those of ordinary skill in the art will appreciate, these peak-to-peak values are computed by simply subtracting the MIN value (presumably, a negative number, or zero) from the MAX value (a positive number, or zero) for each captured beat.

After the computations of peak-to-peak impedance values in block 106, CPU 32 next computes a "control" value, in block 108, which may be the average, minimum, or a percentage of minimum of the peak-to-peak values computed in block 106. After computing the control values in block 108, the next step in the initialization phase, for the atrial chamber only, is to determine whether the patient has A-V conduction, as indicated by block 110 in FIG. 8. Those of ordinary skill in the art will appreciate that this can be accomplished by delivering an atrial pacing stimulus and then monitoring ventricular activity to ascertain whether a ventricular contraction is evoked as a result of the atrial stimulus. The information obtained in block 110 regarding whether the patient has A-V conduction is used during the testing phase of the threshold determination process, as will be hereinafter described in greater detail.

Determining whether the patient has A-V conduction in block 110 completes the initialization phase of the threshold testing process; flow next proceeds to the testing phase, as indicated by block 112.

Figure 9:
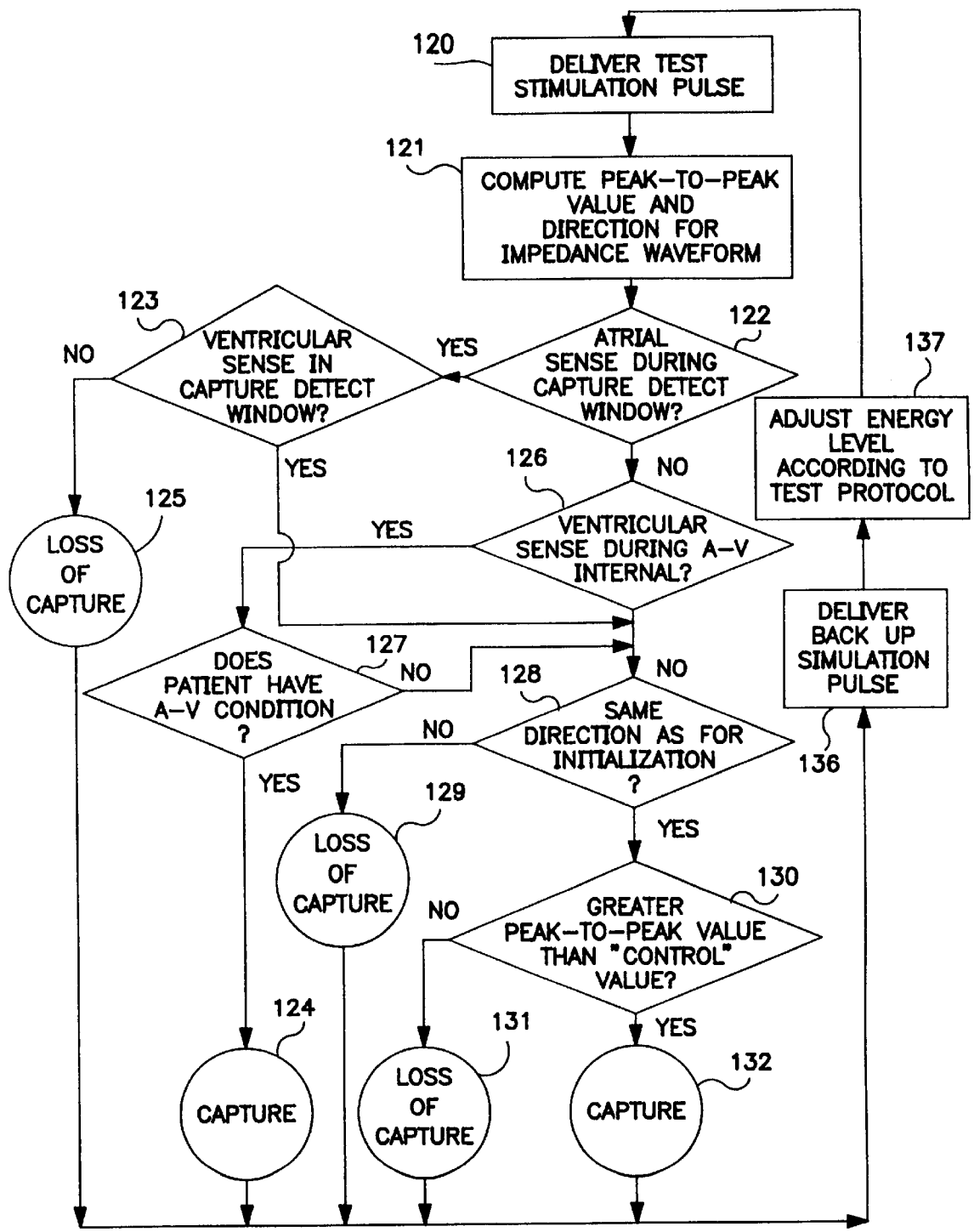
FIG. 9 is a flow diagram showing the steps involved in an atrial threshold testing phase of the capture detection algorithm in accordance with the disclosed embodiment of the invention.
Figure 10:
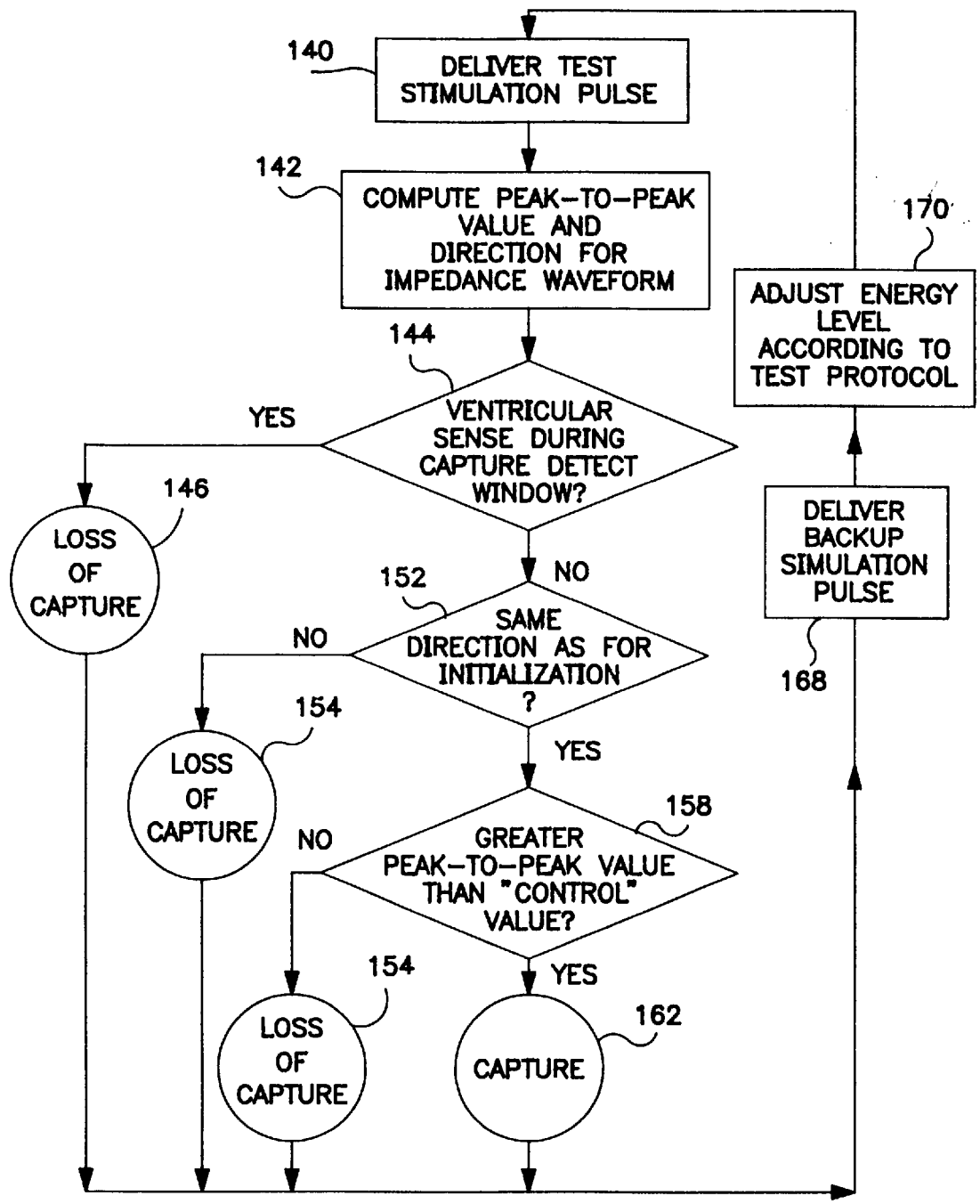
FIG. 10 is a flow diagram showing the steps involved in a ventricular threshold testing phase of the capture detection algorithm in accordance with the disclosed embodiment of the invention.

In accordance with one aspect of the present invention, separate threshold tests are performed for the atrial and ventricular chambers. FIG. 9 is a flow chart illustrating the steps taken during the atrial testing phase of the threshold determination process in accordance with the presently disclosed embodiment of the invention. FIG. 10 is a flow chart illustrating the steps taken during the ventricular testing phase of the threshold determination process in accordance with the presently disclosed embodiment of the invention. Both the atrial and ventricular testing phases consist of the delivery of a series of stimulation pulses of varying energy levels (i.e., of varying pulse widths, and of varying pulse amplitudes), coupled with determinations of whether or not each stimulation pulse has resulted in capture.

In particular, during the testing phase of the threshold testing procedure (for either chamber) the amplitude and pulse width values in the chamber under test begin alternating between programmed test values and backup stimulus values. This results in alternating pairs of pulses—a test pulse followed by a backup pulse, and so on. In this way, patient safety is protected, since capture is ensured for at least every other stimulation pulse.

For each chamber of the heart, the test itself consists of two parts—an amplitude threshold test, and a pulse width threshold test. The amplitude threshold test is performed using a fixed maximum pulse width to determine the threshold amplitude, which is the lowest amplitude which is found to result in capture. Then a series of pulse width threshold tests using increasing amplitude settings are performed to find associated threshold pulse widths, which are the shortest pulse widths which result in capture.

Following each test pulse delivery during the testing phase, pacemaker 10 transmits capture marker information to the external programmer, indicating whether capture was achieved for the latest test pulse.

Referring to the flowchart of atrial threshold determination shown in FIG. 9, the atrial testing phase begins with block 120, wherein an atrial test stimulation pulse is delivered. The amplitude and pulse width of the stimulating pulses delivered during the test phase are varied, as will be described in further detail below. After delivery of a test pulse in block 120, the MAX, MIN, and DIRECTION values are communicated to CPU 32 as described in detail above. Based upon this information, CPU 32 computes peak-to-peak and direction values, as represented by block 121 in FIG. 9. For each atrial test pulse delivered, CPU 32 is also informed, by sense amplifier circuitry 24, whether an atrial event is sensed during the capture detect window and whether a ventricular event is sensed within the A-V interval following delivery of the test pulse.

If an atrial sensed event is detected during the capture detect window associated with a given test pulse (block 122 in FIG. 9), then a determination is made in block 123 whether a ventricular sense occurred during the capture detect window. If not, CPU 32 interprets this as a loss-of-capture, as indicated by block 125. This corresponds to the situation depicted in FIG. 6d. If, on the other hand, a ventricular sense did occur during the capture detect window, flow proceeds from block 123 to block 128, wherein it is determined whether the direction value for the ventricular sense matches that derived during the initialization phase.

Returning to block 122, if no atrial sensed event is detected during the capture detect window, flow proceeds to block 126 in FIG. 9, wherein a determination is made whether a ventricular sensed event was detected during the A-V interval following a given test pulse. If such a ventricular event was sensed, a determination is made whether the patient has A-V conduction, in block 127 (recall that this was determined during the initialization phase, described above with reference to FIG. 8). If the patient does have A-V conduction, CPU 32 interprets this as indicating capture, as shown in block 124.

If, in block 123, it is determined that a ventricular sense did occur during the capture detect window (block 123), or, in block 127, if the patient does not have A-V conduction, or, in block 126, it is determined that no ventricular sense occurred during the A-V interval, flow proceeds to block 128 in FIG. 9, wherein as noted above a determination is made by CPU 32 whether the direction value for the test pulse matches the direction values for each of the pulses delivered during the initialization phase (as noted above, all direction values during the initialization phase are required to be the same before the testing phase can begin). If the direction value for the stimulation pulse delivered in block 120 does not match the initialization value, this is taken as an indication of loss-of-capture (LOC), as represented by outcome block 129 in FIG. 9.

If the direction value for the test pulse delivered in block 120 is found in block 128 to be the same as for the initialization phase, flow proceeds to block 130, wherein CPU 32 determines whether the peak-to-peak value computed in block 122 is greater than the "control" value computed during the initialization phase. If not, this is taken as a loss-of-capture, as represented by outcome block 131 in FIG. 9. If the peak-to-peak value computed in block 122 is greater than the control value, however, this is taken as an indication of capture, as indicated by outcome block 132 in FIG. 9.

With continued reference to FIG. 9, after a determination of loss-of-capture is made in outcome blocks 125, 129, or 131, or after a determination of capture in blocks 127 or 132, flow next proceeds to block 136, wherein a "backup" pulse is delivered. The amplitude and pulse width of the backup pulse delivered in block 136 are set to predetermined levels sufficiently far above minimum to ensure that capture will be achieved. Delivery of a backup pulse (block 136) after every test pulse (block 120) ensures that even if the pulse delivered in block 120 fails to achieve capture, at least every other pulse delivered during the test phase will achieve capture.

Following delivery of a backup pulse in block 136, the energy level for the next test pulse to be delivered is adjusted according to the corresponding protocol (either amplitude testing or pulse width testing, as described below), as indicated by block 137 in FIG. 9. Thereafter, the test cycle is repeated, beginning with block 120, with varying amplitude and/or pulse width settings for the test pulse as will be described in greater detail below.

Turning now to FIG. 10, there is provided a flow chart illustrating the steps involved in ventricular threshold determination in accordance with the presently disclosed embodiment of the invention. Like the atrial test, the ventricular test in FIG. 10 begins with the delivery of a test stimulation pulse, in block 140, and the computation of peak-to-peak and direction values for the stimulation pulse, in block 142. These values, along with indications of sensed events during the capture detect window following the test pulse, are communicated to CPU 32.

As indicated by decision block 144 in FIG. 10, CPU 32 first determines whether a ventricular event was sensed during the capture detect window following a ventricular test pulse. If a ventricular event was sensed, this is taken as an indication of loss-of-capture, as represented by outcome block 146. This corresponds to the situation depicted in FIG. 7*a*. If not, flow proceeds to block 152 in FIG. 10, wherein the DIRECTION value for the test pulse is compared with the control direction value. If these values are different, this is taken as an indication of loss-of-capture, as indicated by outcome block 154. Otherwise, the peak-to-peak value for the test pulse is compared with the control value derived during the initialization phase, as indicated by decision block 158. If the peak-to-peak value is less than the control value, this is interpreted as an indication of loss-of-capture, as represented by outcome block 160. If the peak-to-peak value is greater than the control value, however, this is interpreted as indicating capture, as represented by outcome block 162 in FIG. 10.

Whether loss-of-capture (in blocks 146, 154, or 160) or capture (block 162) is found, flow next proceeds to block 168, wherein a backup stimulation pulse is delivered, just as in the case of atrial testing. Next, in block 170, the energy level for the next test pulse is adjusted according to the test protocol (to be described in greater detail below). Then, the test cycle is repeated, beginning with block 140.

The processes outlined in FIGS. 9 and 10 are used for both the amplitude threshold test and for the pulse width threshold test portions of the test phase. During the amplitude threshold test for a given chamber of the heart, the stimulation pulse width is maintained at a constant value (1.5-mSec in the preferred embodiment), while the pulse amplitude is varied.

For both chambers of the heart, the amplitude threshold step consists of the following three steps (it is to be understood for the purposes of the following description that a backup pulse is delivered after every two test pulse):

AMPLITUDE TEST STEP 1

The amplitude is decreased by 0.5-V, and two test pulses are delivered at this reduced amplitude. If capture is achieved by both of these test pulses, this step is repeated until either the minimum allowable amplitude (0.5-V in the preferred embodiment) is reached or until loss-of-capture is detected. If the minimum amplitude is reached, this amplitude is used for the pulse-width threshold test to be hereinafter described.

AMPLITUDE TEST STEP 2

The test pulse amplitude is set to the backup pulse value for one or more test pulses (this number preferably being among the programmably selectable parameters of the device). Then, a test pulse with an amplitude 0.5-V greater than the pulse which failed to achieve capture in step 1 is delivered. This step is repeated until capture is achieved or until the maximum pulse amplitude is reached.

AMPLITUDE TEST STEP 3

Additional test pulses with the same amplitude as the pulse which achieved capture in step 2 are delivered (again, this number of such additional pulses preferably being among the programmably selectable parameters of the device). If either of these test pulses fails to achieve capture, steps 2 and 3 are repeated. If both achieve capture, this amplitude is said to be the patient's amplitude threshold.

Figure 11:
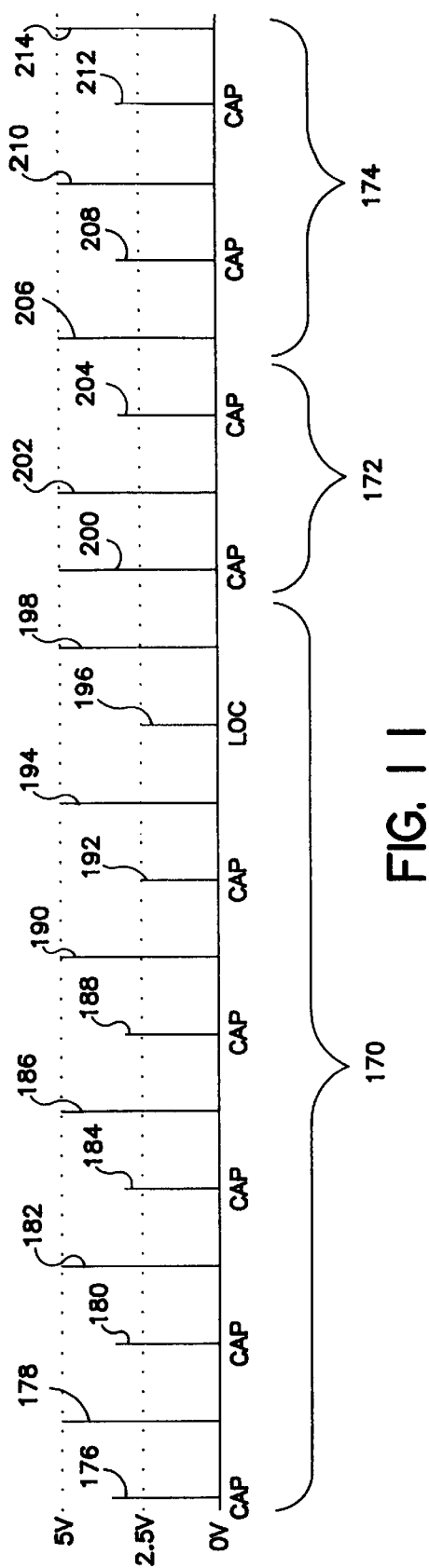
FIG. 11 is a timing diagram showing the delivery of cardiac stimulation pulses of varying amplitudes over time.

FIG. 11 is a timing diagram illustrating the timing and amplitude of stimulation pulses delivered during an exemplary amplitude threshold test. Referring to FIG. 11, bracketed portions 170, 172, and 174 correspond to steps 1, 2, and 3 above, respectively.

The first step 170 of test begins with the delivery of a first test pulse, designated with reference numeral 176 in FIG. 11, which has an amplitude that is reduced by 0.5-V from the programmed value prior to initiation of the amplitude threshold test. In FIG. 11, the initial amplitude was 4.0-V, and the amplitude of test pulse 176 is 3.5-V. Following delivery of test pulse 176, a backup pulse 178 is delivered. In the presently preferred embodiment, the amplitude of backup pulses is the minimum of: (programmed amplitude plus 2.0-V) and (5.0-V).

During the first step 170 of the amplitude threshold test, whenever a test pulse is found to achieve capture (and a subsequent backup pulse is delivered), a second test pulse having the same amplitude is delivered before the test pulse amplitude is incrementally reduced. As shown in FIG. 11, test pulse 176 is found to achieve capture, so that after delivery of backup pulse 178, a second test pulse 180 having the same amplitude of test pulse 176 is delivered. After delivery of test pulse 180, a backup pulse 182 is delivered.

Since test pulse 180 achieved capture, the next test pulse 184 after backup pulse 182 has an amplitude 3.0-V, i.e., 0.5-V less than test pulses 176 and 180. Test pulse 184 is found to achieve capture; therefore, following the delivery of a backup pulse 186, a second 3.0-V test pulse 188 is delivered, followed by another backup pulse 190. Test pulse 188 also achieves capture, so the process of incrementally reducing the test pulse amplitude is repeated, resulting in the delivery of a 2.5-V test pulse 192, a backup pulse 194, another 2.5-V test pulse 196, and another backup pulse 198.

In accordance with the presently disclosed embodiment of the invention, the process of incrementally reducing the test pulse amplitude after two test pulses of a given amplitude are found to achieve capture is repeated either until the minimum allowable pulse amplitude (0.5-V in the presently preferred embodiment) is reached, or until loss-of-capture is detected. In the timing diagram of FIG. 11, test pulse 196 is the first to result in loss-of-capture during the first step 170 of the amplitude threshold test. As a result, the second step 172 of the amplitude threshold test is begun following delivery of backup pulse 198.

During the second step 172 of the amplitude threshold test of FIG. 11, test pulses 200 and 202 having the backup pulse amplitude is delivered. (Although only two pulses 200 and 202 are shown in FIG. 11, the number of such pulses is preferably among the programmable parameters of device 10.) This protocol results in multiple (three, in FIG. 11) pulses having the backup amplitude (i.e., pulses 198, 200, and 202) being delivered following loss of capture during the first step 170 of the amplitude threshold test. This ensures that capture will be regained following loss of capture, and advantageously stabilizes the patient's hemodynamics and hence the impedance signal.

Second step 172 of the amplitude threshold test next involves delivery of a test pulse 204 having an amplitude 0.5-V higher than pulse 196, the test pulse which failed to achieve capture. A backup pulse 206 is then delivered. If capture is not detected for pulse 204 with the increased amplitude, the amplitude of the next test pulse after backup pulse 206 would be increased by another 0.5-V increment, and this incremental increasing would be repeated until capture was achieved. In FIG. 11, however, test pulse 204 does achieve capture, so the third step 174 of the amplitude threshold test is begun.

In third step 174, more test pulses (in the example of FIG. 11, pulses 208 and 212, but possibly more depending upon device programming) with the same increased amplitude as test pulse 204 are delivered (with two intervening backup pulses 206 and 210).

If either of the two test pulses delivered during the third step 174 of the test fail to achieve capture, second and third steps 172 and 174 of the amplitude threshold test are immediately repeated, i.e., the amplitude of the test pulse is increased by 0.5-V until capture is achieved, and then two additional test pulses at this increased amplitude are examined to confirm that capture is achieved.

Since, in the example of FIG. 11, test pulses 208 and 212 do achieve capture, this concludes the amplitude threshold test phase. The amplitude of test pulses 208 and 212 is referred to as the patient's amplitude threshold. Next, the pulse width testing phase is begun.

As previously noted, the pulse width of test pulses during the amplitude threshold test is maintained at a constant 1.5-mSec. The pulse width test phase begins with the test pulse amplitudes being maintained at the threshold level determined during the amplitude threshold test phase, while the pulse widths of test pulses are varied. (It is to be understood for the purposes of the following description that a backup pulse is delivered after every test pulse.)

The pulse width threshold test is similar to the amplitude threshold test, and consists of four steps:

PULSE WIDTH TEST STEP 1

The pulse width of the first test pulse in the pulse width threshold test is set to 0.75-mSec (i.e., one half of the pulse width value used during the amplitude threshold test) and the pulse amplitude of the test pulse is set to the amplitude threshold determined during the amplitude threshold test. If this test pulse is found to achieve capture, another test pulse is delivered with the same pulse width. If this second test pulse also achieves capture, the pulse width is decreased by a predetermined amount, and this is repeated until the minimum allowable pulse width (0.06-mSec in the preferred embodiment) is reached.

PULSE WIDTH TEST STEP 2

If after decreasing the pulse width in step 1, a test pulse fails to achieve capture, the test pulse width is set to the backup value for one or more test pulses. Then, the pulse width is set to 0.06-mSec greater than the width which failed to achieve capture. (As for the amplitude threshold test, setting the pulse width to the backup value for one or more test pulses ensures that three or more pulses with the backup settings will be delivered following loss of capture, so that capture will be regained.)

If capture does not occur for the increased pulse width, STEP 2 is repeated, i.e., the pulse width it is increased again by 0.06-mSec increments until capture is achieved.

PULSE WIDTH TEST STEP 3

Once an increased pulse width does achieve capture in step 2, the next two or more consecutive test pulses (this value being a programmable parameter) are examined for capture. If any of these two fail to achieve capture, steps 2 and 3 above are repeated. If capture is achieved by each of the pulses in this step, step 3 is deemed completed.

PULSE WIDTH TEST STEP 4

As noted above, steps 1 through 3 of the pulse width threshold test are performed with the test pulse amplitude maintained at the patient's amplitude threshold, determined during the amplitude threshold testing phase previously described with reference to FIG. 11.

Step 4 of the pulse width test involves repeatedly incrementing the test pulse amplitude value by 0.5-V and performing pulse width test steps 1 through 3 for each successively higher test pulse amplitude values. In particular, steps 1 through 3 are repeated four times or until the amplitude reaches 5-V (whichever is first). As described above, each iteration of steps 1 through 3 yields an amplitude/pulse width value data pair, e.g., a unique pulse width threshold value associated with various amplitude values ranging between the patient's amplitude threshold (determined as described above during the amplitude threshold testing phase) and 5-V. The starting pulse width for each iteration is the pulse width used at the end of the previous iteration. As these iterations of pulse width tests are performed, the data pairs so obtained are compiled in memory circuit 30 associated with CPU 32.

Upon completion of the pulse width threshold testing phase (i.e., after multiple iterations of pulse width test steps 1 through 3), the data pairs stored in memory 30 are preferably transmitted to an external pacing controller/programmer unit. This data can be used to generate a so-called strength-duration curve, which relates amplitude to pulse width for the patient. An example strength-duration curve is graphically depicted in FIG. 12.

Figure 12:
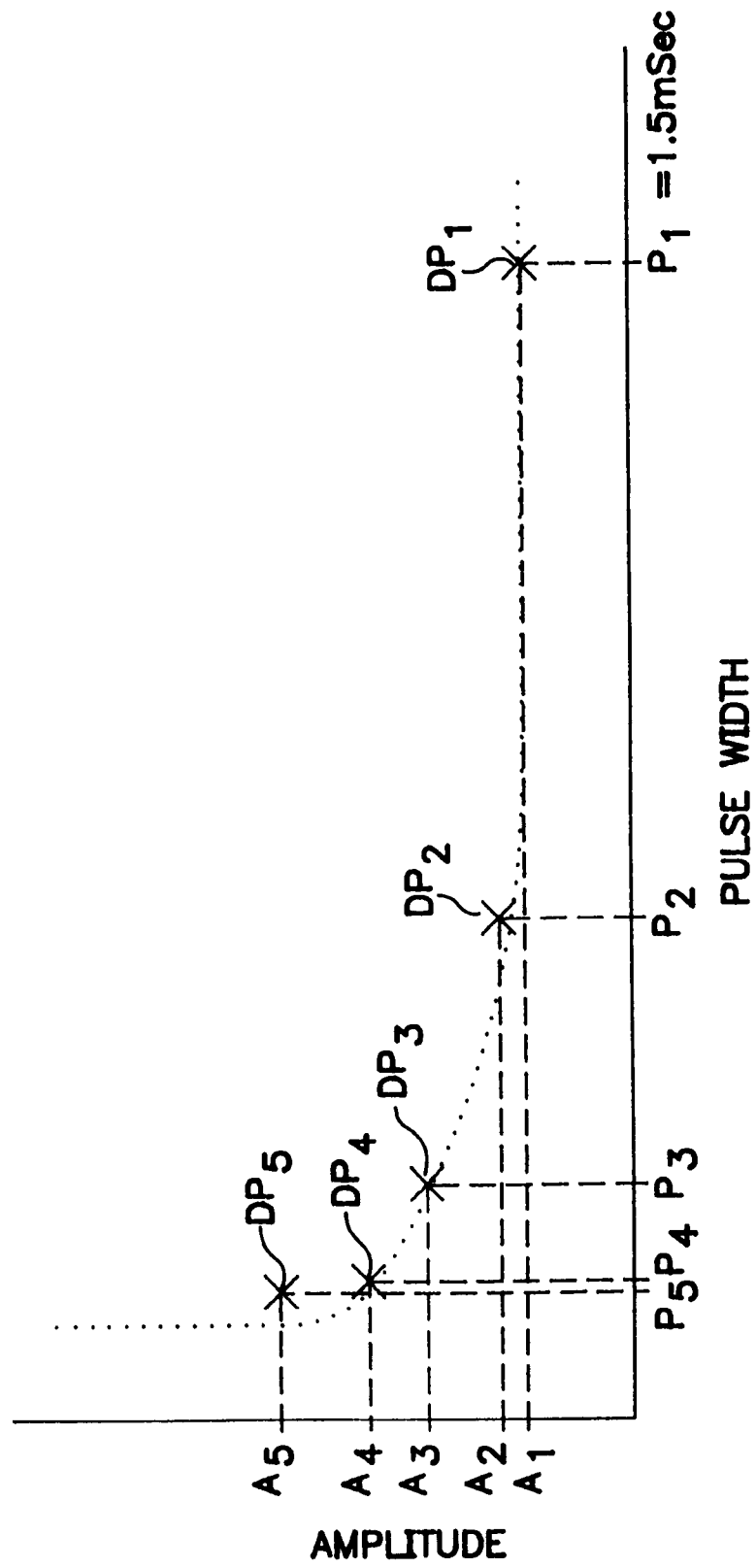
FIG. 12 is a strength-duration curve derived from data provided by the pacemaker of FIGS. 1 and 2 in accordance with the disclosed embodiment of the invention.

As shown in FIG. 12, pulse width data for a strength-duration curve is plotted along the horizontal axis, while amplitude data is plotted along the vertical axis. A first data point, designated $DP_1$ in FIG. 12, represents the threshold measurement obtained during the amplitude threshold test, and as such represents the point on the patient's strength-duration curve corresponding to pulse width $P_1$. In the case of the curve shown in FIG. 12, the patient exhibited an amplitude threshold of $A_1$ for a pulse width of $P_1=1.5$-mSec.

A second data point $DP_2$ in FIG. 12 reflects the data pair obtained during the first iteration of the pulse width threshold test phase, wherein amplitude $A_2$ is incrementally increased by 0.5-V from its initial level. For amplitude $A_2=A_1+0.5$-V, the patient whose strength-duration curve is depicted in FIG. 12 exhibited a pulse width threshold of $P_2$, where (as those of ordinary skill in the art would expect), $P_2<P_1$. This reflects the expected situation where a stimulation pulse of higher amplitude needs a shorter pulse width to achieve capture than does a pulse of relatively lower amplitude.

Similarly, data point $DP_3$ (pulse width $P_3$ and amplitude $A_3=A_2+0.5$-V) in FIG. 12 reflects the data pair obtained during the second iteration of the pulse width testing phase, data point $DP_4$ (pulse width $P_4$ and amplitude $A_4=A_3+0.5$-V) reflects the data pair obtained during the third iteration of the pulse width testing phase, and data point $DP_5$ (pulse width $P_5$ and amplitude $A_4=A_3+0.5$-V).

In the presently preferred embodiment, once the strength-duration data is transmitted to the external programming unit (such as the Medtronic Model 9790 or the like), the programmer software generates a strength-duration curve similar to that depicted in FIG. 12 and presents the graph to the physician or clinician on a graphics display. It is contemplated that the programmer can be capable of employing any one of several known curve-fitting algorithms in the course of deriving the strength-duration graph. It is further contemplated that the programmer can compute and present to the physician or clinician recommended output settings after applying predetermined safety margin criteria to the strength-duration data obtained from the pulse amplitude and pulse width threshold tests described above.

From the foregoing detailed description of a specific embodiment of the invention, it should be apparent that a method and apparatus for automatically determining a patient's cardiac stimulation threshold has been disclosed. The present invention encompasses a method and apparatus for enhanced capture determination based upon measurements of two or more detectable physioligical characteristics, whereby capture and loss-of-capture can be reliably and accurately distinguished.

Although a specific embodiment of the invention has been described herein in some detail, this has been done solely for the purposes of illustrating the invention in its various aspects and is not intended to be limiting with respect to the scope of the invention. It is contemplated that various alterations, substitutions, and/or modifications, including but not limited to those alternatives and options specifically mentioned herein, may be made to the disclosed embodiment without departing from the spirit and scope of the invention as defined in the appended claims which follow. The inventors in particular contemplate adaptation of the invention as described in connection with a specific embodiment herein to integrate cardiac pressure sensing, blood oxygen saturation measurement, or the like into the redundant sensing protocol, rather than impedance sensing. That is, it is believed that those of ordinary skill in the art having the benefit of the present disclosure could implement an automatic threshold determination function in a pacemaker having cardiac pressure (or oxygen saturation) measurement capabilities rather than impedance measurement capabilities as in the disclosed embodiment.

What is claimed is:

1. A pacemaker system comprising:
    a body-implantable pulse generator;
    at least one conductive lead having a distal end and a proximal end, said proximal end for coupling to said pulse generator and having at least one lead electrode disposed near said distal end for placement within a chamber of a patient's heart, said lead having conductor means adapted to deliver stimulating pulses to said heart and to convey cardiac electrical signals from said electrode to said pulse generator;
    a common electrode, coupled to said pulse generator;
    said pulse generator comprising:
        a control circuit having signal generating means for issuing control signals including an excitation control signal for timing excitation pulses, a capture detect window signal for timing a capture detect window, and at least one stimulation control signal for timing and controlling pulse width and amplitude for stimulation pulses;
        a stimulation circuit, coupled to said control circuit and to said lead, responsive to said at least one stimulation control signal to generate a stimulation pulse having amplitude and pulse width determined by said at least one stimulation control signal;
        an excitation circuit, coupled to said control circuit, said common electrode, and said lead, said control circuit being responsive to said excitation control signal to generate excitation pulses to be applied to said heart via said lead;
        an impedance circuit, coupled to said control circuit and to said lead and responsive to assertion of said capture detect window signal following generation of a stimulation pulse by said stimulation circuit to derive a cardiac impedance signal reflecting a voltage differential between said lead electrode and said common electrode;
        an impedance processing circuit, coupled to said impedance circuit and to said control circuit and responsive to said capture detect window signal to derive at least one morphology value reflecting morphology of said impedance signal so as to characterize said impedance signal with said morphology value;
    wherein said control circuit comprises a control value reading circuit for reading at least one control value and comparator means to compare said at least one morphology value to said at least one control value to determine whether said stimulation pulse achieved cardiac capture.

2. A pacemaker system as set forth in claim 1 wherein said at least one morphology value derived by said impedance processing circuit is a measure of said impedance signal direction.

3. A pacemaker system as set forth in claim 2 wherein said comparator means further comprises a mechanism for comparing a second morphology value to a second control value and wherein said impedance processing circuit derives said second morphology value and said second morphology value is peak to peak amplitude.

4. A pacemaker system in accordance with claim 1, wherein said common electrode comprises a conductive canister containing said pulse generator.

5. A pacemaker system in accordance with claim 1, wherein said at least one morphology value derived by said impedance processing circuit comprises a digital value corresponding to the peak-to-peak amplitude of an excursion of said impedance signal.

6. A pacemaker system in accordance with claim 1, further comprising:

said body implantable pulse generator further comprising;

telemetry trancieving circuitry for recieving telemetry signals and communicating a signal representative of said telemetry signals to said control circuit and for transmitting signals representative of signals indicative of operational characteristics of said body implantable pulse generator and of physiologic conditions of a body into which said body implantable pulse generator may be implanted, said control circuit further comprising control logic means for receiving and selectively altering operations based on command and parameter signals it may receive through said telemetry receiving means from an external source such as an external programming unit, and an external programming unit, comprising a memory circuit linked to a first telemetry transmitter and receiver circuit, for transmitting said command signals and said parameter value signals to said body-implantable pulse generator and for receiving said signals indicative of operational characteristics and said physiologic conditions signals from said body-implantable pulse generator.

7. A pacemaker system in accordance with claim 6, wherein said external programming unit further comprises an external programming unit control circuit means for causing said transmission circuit to transmit a sequence of command and parameter value signals to said body-implantable pulse generator, such that said pulse generator delivers a sequence of stimulation pulses in a test sequence having successively lower energy levels to said heart until said control circuit determines that one of said test stimulation pulses does not achieve capture.

* * * * *